(12) United States Patent
Kim et al.

(10) Patent No.: US 10,088,175 B2
(45) Date of Patent: Oct. 2, 2018

(54) AIR CONDITIONER

(71) Applicant: LG ELECTRONICS INC., Seoul (KR)

(72) Inventors: Taeyoung Kim, Seoul (KR); Gyoungsoo Kim, Seoul (KR); Jaeyoul Joung, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 15/368,920

(22) Filed: Dec. 5, 2016

(65) Prior Publication Data

US 2018/0023820 A1    Jan. 25, 2018

(30) Foreign Application Priority Data

Jul. 22, 2016    (KR) .................. 10-2016-0093718

(51) Int. Cl.
*F24F 1/00* (2011.01)
*F24F 13/30* (2006.01)
(Continued)

(52) U.S. Cl.
CPC .............. *F24F 1/0007* (2013.01); *A61L 9/20* (2013.01); *F24F 1/0025* (2013.01); *F24F 13/20* (2013.01);
(Continued)

(58) Field of Classification Search
CPC .................................. A61L 9/20; A61L 9/205
See application file for complete search history.

(56) References Cited

U.S. PATENT DOCUMENTS 5,043,634 A    8/1991    Rothwell, Jr.
5,353,085 A    10/1994   Kurematsu
(Continued)

FOREIGN PATENT DOCUMENTS

KR    10-2003-0091688    12/2003
KR    10-2005-0083416    8/2005
(Continued)

OTHER PUBLICATIONS

U.S. Office Action dated Aug. 3, 2017 issued in U.S. Appl. No. 15/363,071.
(Continued)

*Primary Examiner* — Phillip A Johnston
*Assistant Examiner* — Hsien Tsai
(74) *Attorney, Agent, or Firm* — KED & Associates LLP

(57) ABSTRACT

An air conditioner is provided that may include a main body having an air inlet and an air outlet defined therein; a filter received in the main body to filter air suctioned into the main body; a heat exchanger configured to perform a heat exchange between a refrigerant and the air suctioned into the main body; and an ultraviolet (UV) sterilization module configured to sterilize the air suctioned into the main body. The UV sterilization module may include a porous main body in a mesh form, and a plurality of UV lamps. The porous main body may include a bent portion to allow the porous main body to conform to a shape of the heat exchanger. The main body may include a chassis, and a front frame at a front of the chassis. An inner space may be defined between the chassis and the front frame. The porous main body may be coupled to at least one of the chassis or the front frame, and the plurality of UV lamps may be arranged to be spaced from each other between the air inlet and the heat exchanger.

20 Claims, 29 Drawing Sheets

(51) Int. Cl.
*F24F 13/28* (2006.01)
*F24F 13/20* (2006.01)
*F24F 13/22* (2006.01)
*A61L 9/20* (2006.01)

(52) U.S. Cl.
CPC ............ *F24F 13/222* (2013.01); *F24F 13/28* (2013.01); *F24F 13/30* (2013.01); *A61L 2209/14* (2013.01); *F24F 2001/0048* (2013.01)

(56) References Cited

U.S. PATENT DOCUMENTS

| | | | |
|---|---|---|---|
| 5,558,158 A * | 9/1996 | Elmore | ................. A61L 9/20 165/122 |
| 5,879,435 A | 3/1999 | Satyapal | |
| 5,993,749 A | 11/1999 | Adams | |
| 6,685,890 B1 | 2/2004 | Van Remmen | |
| 7,773,081 B2 | 8/2010 | Olson | |
| 7,852,005 B2 | 12/2010 | Misono et al. | |
| 8,018,130 B2 | 9/2011 | Van Den Broek et al. | |
| 8,124,012 B2 | 2/2012 | Leroux et al. | |
| 8,232,715 B2 | 7/2012 | Kusunoki et al. | |
| 8,269,420 B2 | 9/2012 | Morizawa et al. | |
| 8,304,974 B2 | 11/2012 | Watanabe et al. | |
| 8,475,725 B1 | 7/2013 | Antipenko et al. | |
| 9,182,135 B2 | 11/2015 | Rothfuss | |
| 9,518,487 B2 | 12/2016 | Coelho | |
| 9,873,128 B2 | 1/2018 | Kim | |
| 9,895,462 B2 | 2/2018 | Law | |
| 9,963,017 B2 | 5/2018 | Kim | |
| 9,974,881 B2 | 5/2018 | Kim | |
| 2001/0023593 A1 | 9/2001 | Sato | |
| 2001/0025570 A1 | 10/2001 | Fukushima | |
| 2003/0042197 A1 | 3/2003 | Kondou | |
| 2003/0099569 A1 | 5/2003 | Lentz | |
| 2003/0180200 A1 | 9/2003 | Reisfeld | |
| 2003/0217561 A1 | 11/2003 | Shindo et al. | |
| 2003/0230477 A1 * | 12/2003 | Fink | ................. A61L 9/015 204/157.3 |
| 2004/0007000 A1 | 1/2004 | Takeda | |
| 2004/0018125 A1 | 1/2004 | Yang | |
| 2004/0140269 A1 | 7/2004 | Chang | |
| 2004/0200228 A1 | 10/2004 | Yanagimachi | |
| 2004/0226813 A1 | 11/2004 | Wang | |
| 2004/0232846 A1 | 11/2004 | Fischer et al. | |
| 2004/0251810 A1 | 12/2004 | Hsu | |
| 2005/0186124 A1 * | 8/2005 | Fink | ................. A61L 9/205 422/121 |
| 2005/0204713 A1 | 9/2005 | Wu | |
| 2005/0238551 A1 | 10/2005 | Snyder | |
| 2006/0000360 A1 | 1/2006 | Shou | |
| 2006/0016336 A1 | 1/2006 | Taylor | |
| 2006/0016337 A1 | 1/2006 | Taylor | |
| 2006/0018808 A1 | 1/2006 | Taylor | |
| 2006/0018810 A1 | 1/2006 | Taylor | |
| 2006/0021375 A1 | 2/2006 | Wetzel | |
| 2006/0096459 A1 | 5/2006 | Iwano et al. | |
| 2006/0113885 A1 | 6/2006 | Iimura | |
| 2006/0263275 A1 | 11/2006 | Lobach | |
| 2006/0278075 A1 | 12/2006 | Blackner | |
| 2007/0020159 A1 | 1/2007 | Tsui | |
| 2008/0030654 A1 | 2/2008 | Slutsky et al. | |
| 2008/0073565 A1 * | 3/2008 | Jeon | ................. A61L 9/205 250/455.11 |
| 2008/0092742 A1 | 4/2008 | Marra | |
| 2008/0112845 A1 | 5/2008 | Dunn | |
| 2008/0274018 A1 | 11/2008 | Kawai et al. | |
| 2008/0286163 A1 * | 11/2008 | Garfield | ................. A61L 9/205 422/120 |
| 2009/0010801 A1 | 1/2009 | Murphy | |
| 2009/0168433 A1 | 7/2009 | Frick | |
| 2009/0202397 A1 | 8/2009 | Parker | |
| 2010/0047115 A1 | 2/2010 | Krichtafovitch | |
| 2010/0106787 A1 | 4/2010 | Grohman | |
| 2010/0134000 A1 | 6/2010 | Carter et al. | |
| 2010/0150793 A1 | 6/2010 | Chan | |
| 2011/0227501 A1 | 9/2011 | Awamoto et al. | |
| 2012/0085927 A1 | 4/2012 | Maeng et al. | |
| 2012/0153804 A1 | 6/2012 | Li | |
| 2012/0171945 A1 | 7/2012 | Lee | |
| 2012/0199005 A1 | 8/2012 | Koji et al. | |
| 2012/0319011 A1 | 12/2012 | Brabham et al. | |
| 2013/0192288 A1 | 8/2013 | Willette | |
| 2014/0157989 A1 | 6/2014 | Kirschman | |
| 2014/0178254 A1 | 6/2014 | Tsui | |
| 2015/0228470 A1 | 8/2015 | Ruiz | |
| 2015/0262780 A1 | 9/2015 | Eaton | |
| 2016/0243559 A1 | 8/2016 | Kim | |
| 2018/0021468 A1 | 1/2018 | Kim | |
| 2018/0021469 A1 | 1/2018 | Kim | |
| 2018/0021470 A1 | 1/2018 | Kim | |
| 2018/0023820 A1 | 1/2018 | Kim | |
| 2018/0023821 A1 | 1/2018 | Kim | |
| 2018/0104374 A1 | 4/2018 | Kim | |

FOREIGN PATENT DOCUMENTS

| | | |
|---|---|---|
| KR | 10-2006-0035144 | 4/2006 |
| KR | 10-2006-0039360 | 5/2006 |
| KR | 10-0725763 | 5/2007 |

OTHER PUBLICATIONS

U.S. Appl. No. 15/299,622, filed Oct. 21, 2016, Kiet Tuan Nguyen.
U.S. Appl. No. 15/363,036, filed Nov. 29, 2016, Allen Schult.
U.S. Appl. No. 15/363,071, filed Nov. 30, 2016, Sean M. Luck.
U.S. Appl. No. 15/371,418, filed Dec. 7, 2016, Antonio R. Febles.
U.S. Office Action issued in U.S. Appl. No. 15/299,622 dated Mar. 26, 2018.
U.S. Office Action issued in U.S. Appl. No. 15/363,036 dated Jun. 27, 2018.

* cited by examiner

AIR CONDITIONER

CROSS-REFERENCE TO RELATED APPLICATION(S)

The present application claims priority under 35 U.S.C. 119 and 35 U.S.C. 365 to Korean Patent Application No. 10-2016-0093718, filed in Korea on Jul. 22, 2016, which is hereby incorporated by reference in its entirety.

BACKGROUND

1. Field

An air conditioner is disclosed herein.

2. Background

Generally, an air conditioner controls at least one of a temperature, a humidity, or a purification of an indoor air to generate a conditioned air to be suitable for a user. The air conditioner may use a refrigerating cycle of a refrigerant to control a temperature, and a humidity. The air conditioner may include a compressor, a condenser, an expander, and an evaporator as a refrigerant flow path. Indoor air may be suctioned via an inlet to the condenser or the evaporator in which the air is subject to heat exchange and then the air may be discharged via an air outlet.

The air conditioner may include a filter or dust collector to control a purification level of the air. Further, indoor air may be suctioned via an air inlet into the air conditioner and then may be purified using a purification unit or device. The purified air may be discharged via an air outlet out of the air conditioner.

Recently, a UV sterilizer device has been provided in the air conditioner to purify the air in the air conditioner. One example of this approach is disclosed in KR application publication No. 10-2006-0035144 published on Apr. 26, 2006, which is hereby incorporated by reference and in which a UV sterilizer device extends along one surface of the heat exchanger. This prior art UV sterilizer device has a large UV lamp, and thus, has a shortcoming in terms of a space efficiency and air channel. When the larger UV lamp is disposed on the surface of the heat exchanger, the air may not be sterilized uniformly along the front of the heat exchanger.

BRIEF DESCRIPTION OF THE DRAWINGS

Embodiments will be described in detail with reference to the following drawings in which like reference numerals refer to like elements, and wherein.

DETAILED DESCRIPTION

Figure 1:
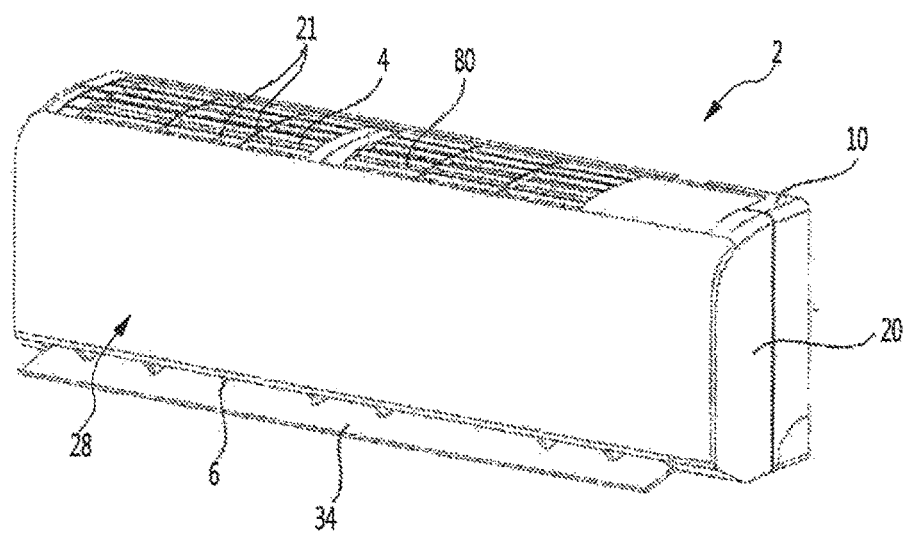
FIG. 1 is a perspective view of an air conditioner according to an embodiment in a turned-on state.

Examples of various embodiments are illustrated in the accompanying drawings and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

Example embodiments will be described in more detail with reference to the accompanying drawings. The present disclosure, however, may be embodied in various different forms, and should not be construed as being limited to only the illustrated embodiments herein. Rather, these embodiments are provided as examples so that this disclosure will be thorough and complete, and will fully convey the aspects and features of the present disclosure to those skilled in the art.

It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, s, operations, elements, and/or components, but do not preclude the presence or addition of one or more other features, integers, s, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Spatially relative terms, such as "beneath," "below," "lower," "under," "above," "upper," and the like, may be used herein for ease of explanation to describe one element or feature's relationship to another element s or feature s as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented for example, rotated 90 degrees or at other orientations, and the spatially relative descriptors used herein should be interpreted accordingly.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description, numerous specific details are set forth in order to provide a thorough understanding of the present disclosure. The present disclosure may be practiced without some or all of these specific details. In other instances, well-known process structures and/or processes have not been described in detail in order not to unnecessarily obscure the present disclosure.

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

Hereinafter, embodiments will be described with reference to attached drawings.

Figure 2:
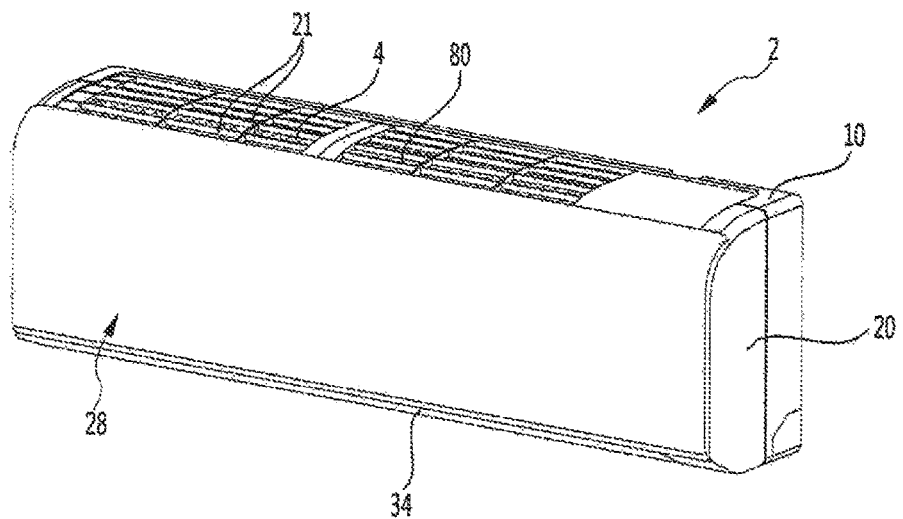
FIG. 2 is a perspective view of the air conditioner according to an embodiment in a turned-off state.
Figure 3:
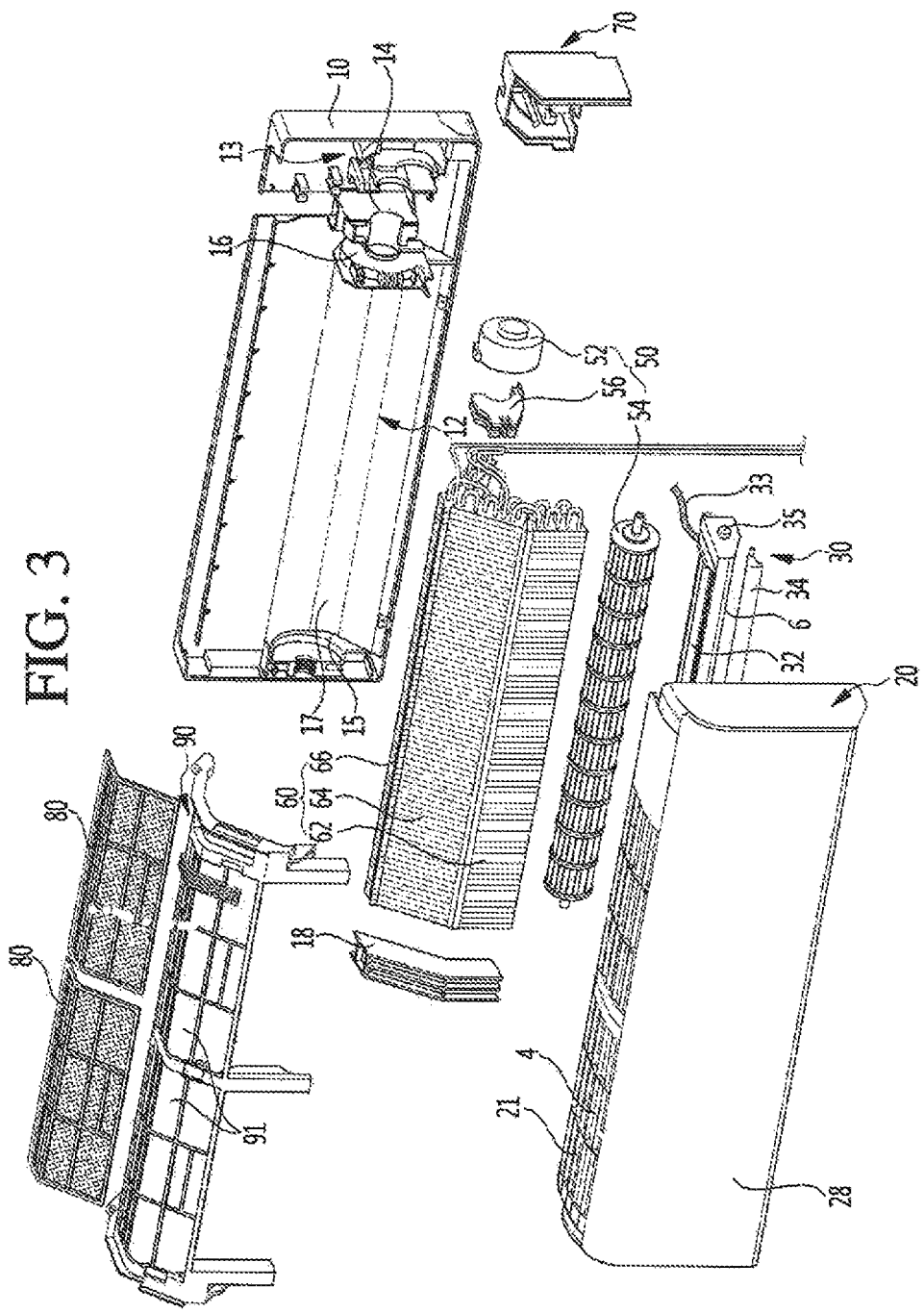
FIG. 3 is an exploded perspective view of the air conditioner according to an embodiment.
Figure 4:
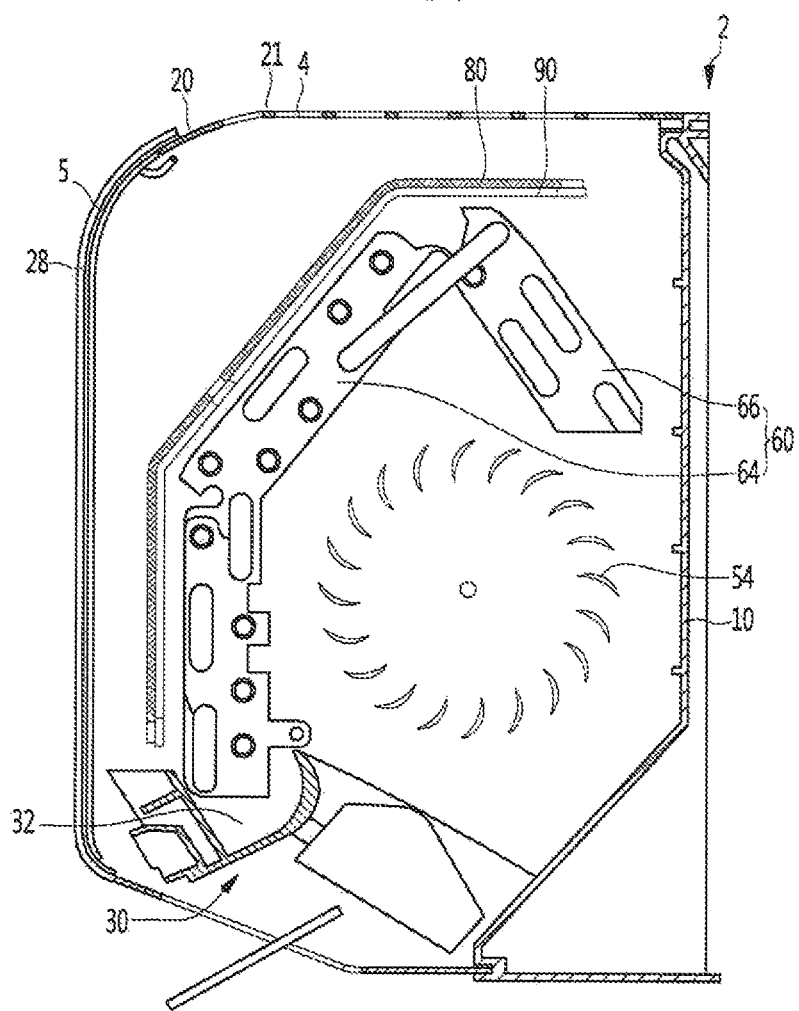
FIG. 4 is a vertical cross-sectional view illustrating a state when a wind-direction adjustment member in FIG. 1 discharges and guides conditioned air to an indoor upper space.

FIG. 1 is a perspective view of an air conditioner according to an embodiment in a turned-on state. FIG. 2 is a perspective view of an air conditioner of FIG. 1 in a turned-off state. FIG. 3 is an exploded perspective view of the air conditioner of FIG. 1. FIG. 4 is a vertical cross-sectional view illustrating a state when a wind-direction adjustment member or adjuster in FIG. 1 discharges and guides a conditioned air to an indoor upper space.

In this embodiment, the air conditioner may include a main body 2 having an air inlet 4 to receive indoor air and an air outlet 6 to discharge conditioned air. In this embodiment, the air conditioner may be configured to receive air from the air inlet 4 and to condition the air therein and then to discharge the conditioned air via the air outlet 6. The air conditioner may be implemented as a stand-type air conditioner, a ceiling-mounted air conditioner, or a wall-mounted air conditioner, for example. Hereinafter, a reference may be made to a wall-mounted air conditioner by way of example.

The main body 2 may be installed or provided Indoors and may be a singular component or a combination of multiple components. In the latter case, the main body 2 may include a chassis 10, a front frame 20, a suction grill 21, a front panel 28, and a discharge unit or device 30. Hereinafter, the chassis 10 may be referred to as a rear frame 10.

In the main body 2, the air inlet 4 may be formed in or at front and top portions thereof and the air outlet 6 may be formed in or at a bottom portion thereof. The front panel 28 may move in a front-rear direction or may pivot downward or upward to form an air suction channel between the front surface and the front panel 28.

Alternatively, in the main body 2, the air inlet 4 may be formed in or at a top portion thereof and the air outlet 6 may be formed in or at a bottom portion thereof. The main body 2 may have an opening for maintenance of the conditioner at the front portion thereof, and the front panel 28 may be arranged to open and close the front surface and the opening of the main body 2.

Hereinafter, a reference will be made to an example in which the air inlet 4 is formed at a top portion of the main body 2, and the air outlet 6 is formed at a bottom portion of the main body 2. The front panel 28 may be formed as a front appearance of the air conditioner and may be configured to pivot around an upper edge thereof or to move in a front-rear direction.

The chassis 10 may be mounted to a wall and may define an air flow channel therein. The chassis 10 may be function as a housing or rear frame to receive various components.

The chassis 10 may have a wind channel guide 12 formed therein to guide an air from the air inlet 4 to the air outlet 6. At one of first and second or left and right sides of the wind channel guide 12, an electronics board 13 may be disposed or provided on which various electronic components may be mounted.

The wind channel guide 12 may define an air channel for a fan 54, which is discussed hereinafter. The wind channel guide 12 may include first and second or left and right guides 15, 16 expanding in a front direction from the chassis 10, and a middle guide 17 between the left and right guides 15, 16. At one of the left and right guide 15, 16, a heat exchanger supporter 18 may be disposed or provided to support a heat exchanger 60 and to define an air channel. From the electronics board 13, a motor installation 14 may protrude in a frontward direction to receive a fan motor 52. On the electronics board 13, a control box 70 may be disposed or provided to control the air conditioner. The control box 70 may be disposed or provided together with a controller (not shown) for the fan motor 52 of an air blower 50, and a wind-direction adjustment member driver 35, for example.

The front frame 20 may be provided at a front of the chassis 10 to define a space with the chassis 10. The front frame 20 may define a wind channel with the wind channel guide 12 of the chassis 10, and may cover the electronics board 13 on the chassis 10 to protect the electronics board 13. The front frame 20 may have openings in top and front portions thereof. The opening in the top portion may act as the air inlet 4. A front opening 5 may act as an access passage for a filter 80 or UV sterilization module or sterilizer 760.

The front frame 20 may have the front opening 5 in a front of the wind channel guide 12 of the chassis 10. An upper opening may be formed at an upper portion in a front of the wind channel guide 12 of the chassis 10.

The suction grill 21 may allow indoor air to be suctioned into the main body 2 and may protect a bottom of the body. The suction grill 21 may be formed in a grill shape on the top opening of the front frame 20.

The discharge unit 30 may discharge conditioned air out of the main body 2. The discharge unit 30 may be assembled to at least one of the chassis 10 or the front frame 20 via a fastener or a hook.

On or at a top of the discharge unit 30, a drain 32 may be provided to collect condensed water falling from the heat exchanger 60. The drain 32 may be coupled to a drain connection hose 33 to guide the condensed water out of the main body 2. The air outlet 6 may be formed on the bottom of the drain 32.

The discharge unit 30 may have a wind-direction adjuster to control a wind-direction of air passing through the air outlet 6. The wind-direction adjuster may guide the air passing through the air outlet 6 and control the wind-direction. The wind-direction adjuster may include a wind-direction adjustment member or adjuster 34 rotatably disposed or provided at the main body 2, more particularly, at the discharge unit 30, and the wind-direction adjustment member driver 35 to rotate the wind-direction adjustment member 34.

The wind-direction adjustment member 34 may include a horizontal wind-direction adjustment member or adjuster to control a horizontal wind-direction of the air passing through the air outlet 6, and a vertical wind-direction adjustment member or adjuster to control a vertical wind-direction of the air passing through the air outlet 6. The wind-direction adjustment member driver 35 may be coupled to the horizontal wind-direction adjustment member to allow the horizontal wind-direction adjustment member to rotate around a vertical axis. Further, the wind-direction adjustment member driver 35 may be coupled to the vertical wind-direction adjustment member to allow the vertical wind-direction adjustment member to rotate around a horizontal axis.

The wind-direction adjustment member 34 may rotate to allow one of the horizontal wind-direction adjustment member or vertical wind-direction adjustment member to open and close the air outlet 6. Hereinafter, a reference will be made to a configuration where the vertical wind-direction adjustment member closes and opens the air outlet 6, the wind-direction adjustment member driver 35 is provided at one of first and second or left and right sides of the discharge unit 30 to drive the rotation of the vertical wind-direction adjustment member as a wind-direction adjustment motor.

The main body 2 may receive the air blower 50 to suction the air into the air inlet 4 and move the air into the main body 2 and discharge the air to the air outlet 6. Further, the main body 2 may receive the heat exchanger 60 to allow heat exchange between the air and refrigerant. Further, the main body 2 may receive the filter 80 to purify the air suctioned into the air inlet 4 and a filter frame 90 for the filter 80.

The air blower 50 may include the fan motor 52 seated in the motor installation 14 formed in the chassis 10, more particularly, the electronics board 13, and the fan 54 disposed or provided at a rotation axis of the fan motor 52 and located on the wind channel guide 12. The fan 54 may be implemented as a horizontally-elongated cross flow fan between the wind channel guides 15,16,17, more particularly, between the left and right channel guides 15,16. The air blower 50 may further include a motor cover 56 disposed or provided at the chassis 10 to cover the fan motor 52.

The heat exchanger 60 may be located between the air inlet 4 and the fan 54. For this, the heat exchanger 60 may be located at a rear of the front frame 20 and may have a lower end disposed or provided on or at a top of the drain 32. The heat exchanger 60 may include a vertical portion 62 on or at the top of the drain 32, a front tilted portion 64 from a top of the vertical portion 62 to a top of a rear portion, and a rear tilted portion 66 from a top of the front tilted portion 64 to a bottom of a rear portion.

The filter frame 90 may be provided between the air inlet 4 and the heat exchanger 60. The filter frame 90 may have openings 91 formed therein to receive the filter 80.

In this embodiment, the air conditioner may include a controller (not shown) provided in the main body 2 to control the fan motor 52, and the wind-direction adjustment member driver 35, for example. The controller may control the fan motor 52 and wind-direction adjustment member driver 35 during an air cooling operation. A cool conditioned air may be guided to the wind-direction adjustment member 34 and then be discharged therefrom. The wind-direction adjustment member 34 may spread the conditioned air via a rotation thereof. In an opening mode of the wind-direction adjustment member driver 35, the wind-direction adjustment member 34 may open the air outlet 6 via a rotation of the wind-direction adjustment member driver 35. The rotation of the fan motor 52 may rotate the fan 54. The rotation of the fan 54 may allow the indoor air to be suctioned via the air inlet 4 into the main body 2 and then to be purified via the filter 80 and then to heat exchange with the heat exchanger 60. Then, the air may pass through the air outlet 6 via the wind-direction adjustment member 34 and then be discharged therefrom.

In a swing discharge mode, the controller may allow forward/reverse rotations of the wind-direction adjustment member driver 35 during the rotation of the fan motor 52. Further, the wind-direction adjustment member 34 may translate vertically via the wind-direction adjustment member driver 35 to allow a vertical spreading of the air passing through the air outlet 6.

Figure 5:
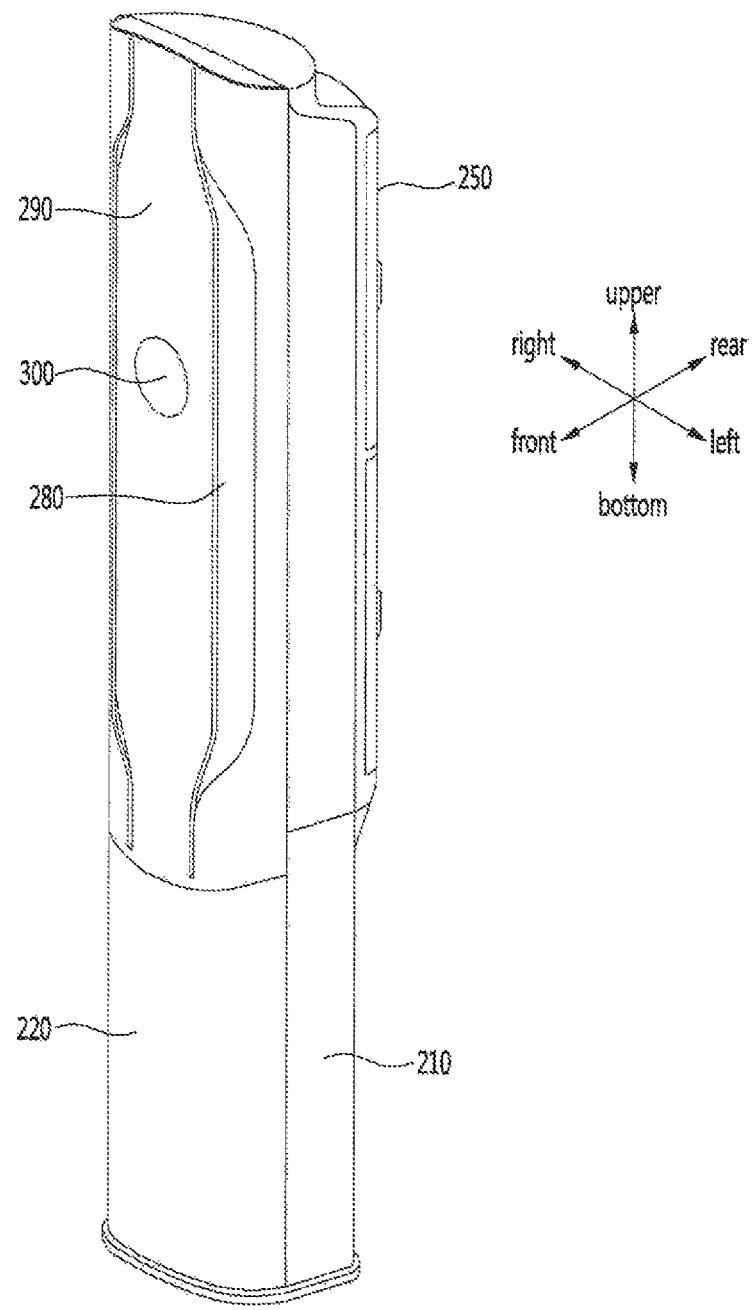
FIG. 5 is a perspective view of an air conditioner according to another embodiment.
Figure 6:
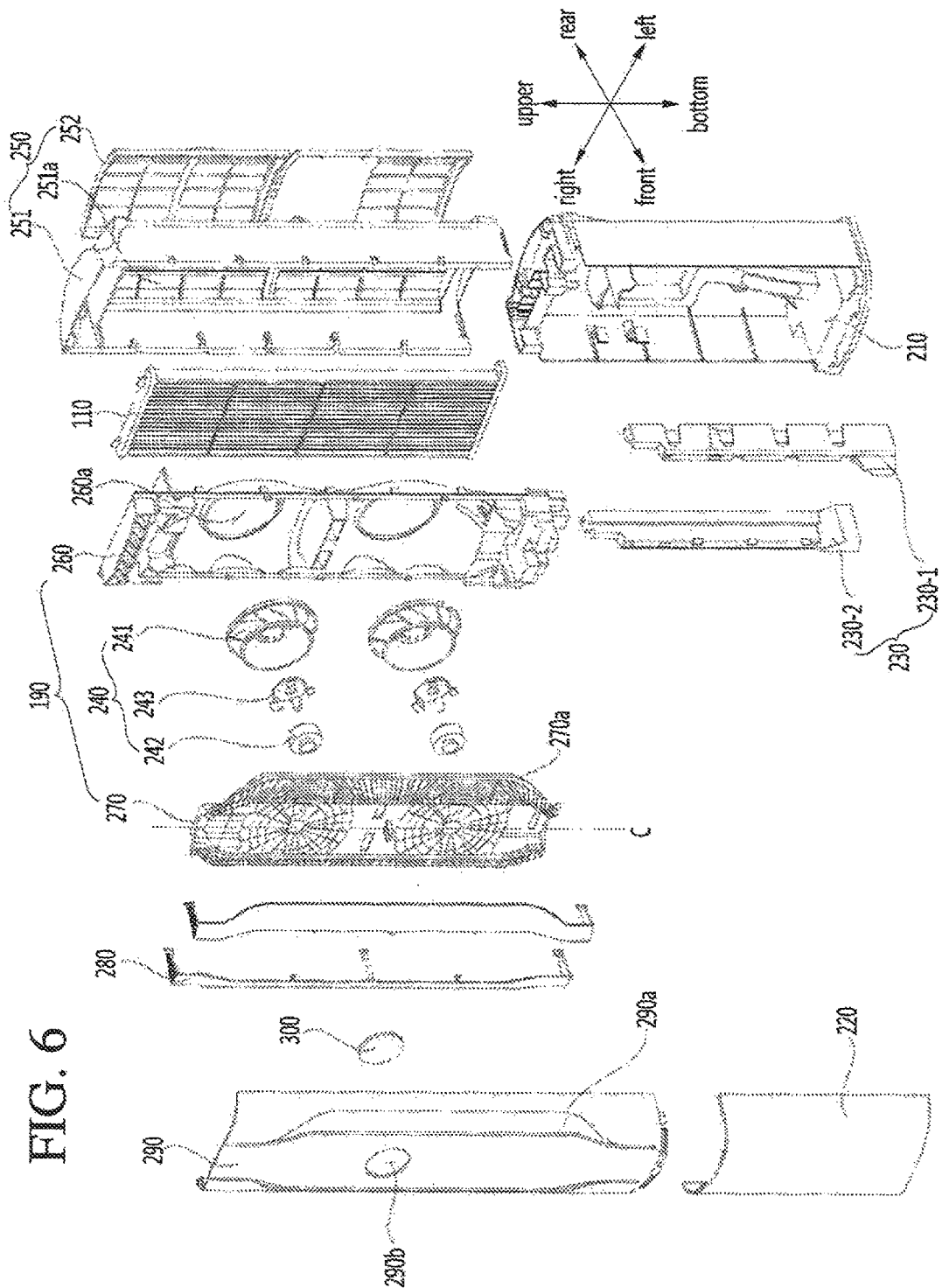
FIG. 6 is an exploded perspective view of the air conditioner of FIG. 5.

FIG. 5 is a perspective view of an air conditioner according to another embodiment. FIG. 6 is an exploded perspective view of the air conditioner of FIG. 5.

In this embodiment, the air conditioner is implemented as a stand-type air conditioner. The stand-type air conditioner may include a base rear panel 210 that contacts a floor and having an inner space therein, and a main body rear panel 250 coupled to a top of the base rear panel 210 and having an air inlet 251*a* formed therein. Further, the stand-type air conditioner may include one or more connector 230 coupled to the base rear panel 210 at an inside thereof, and a base front panel 220 coupled to the connector 230. Further, the stand-type air conditioner may include a main body front panel 290 coupled to the base front panel 220 at a bottom thereof and coupled to the main body rear panel 250 at a side portion thereof and having an air outlet 290a.

The base rear panel 210 may be supported on a floor on which the air conditioner is installed or provided. The base rear panel 210 may have an inner space defined therein. For this, the base rear panel 210 may have a polyhedral shape with an open front portion. The base rear panel 210 may have a curved rear surface. The base rear panel 210 may have a bottom that contacts the floor.

The base rear panel 210 may have an inner side wall coupled to the connector 230. In the inner space in the base rear panel 210, a circuit element to control the air conditioner, and an electronics box (not shown) to receive various electronic components may be provided. The base rear panel 210 may have a front portion coupled to the base front panel 220. The base rear panel 210 may have a top portion coupled to the main body rear panel 250.

The connector 230 may be coupled to the base rear panel 210 at an inner side thereof. The connector 230 may have a vertical elongate column shape. A plurality of the connector 230 may be provided. The plurality of the connector 230 may include a first or left connector 230-1 coupled to an inner first or left surface of the base rear panel 210, and a second or right connector 230-2 coupled to an inner second or right surface of the base rear panel 210. The left connector 230-1 and right connector 230-2 may be horizontally symmetrical.

The connector 230 may reinforce a strength of the base rear panel 210, and may support a shroud panel 260 having one or more air blowing module 240 and a guide panel 270 coupled thereto. The connector 230 may be coupled to the base rear panel 210 at a bottom and a partial side surface of the connector 230. The connector 230 may be coupled to the shroud panel 260 at a top of the connector 230. The connector 230 may be coupled to the base front panel 220 at a front of the connector 230.

The main body rear panel 250 may be coupled to a top of the base rear panel 210 to form an upper rear appearance of the air conditioner. The main body rear panel 250 may be formed of a hollow polyhedral shape with open front and rear surfaces.

The main body rear panel 250 may have the air inlet 251a to suction indoor air therein. The inlet 251a may be formed in a rear portion of the main body rear panel 250. The air blowing module 240 may be turned on to generate an air flow. Thus, the air may be suctioned into the inlet 251a and then the air may pass through an indoor heat exchanger 110 to the shroud panel 260.

The main body rear panel 250 may include a main body rear panel body 251 having the inlet 251a formed at a rear portion thereof, and a rear panel filter 252 mounted to the main body rear panel body 251 at a rear portion thereof to cover the inlet 251a. The rear panel filter 252 may filter the suctioned air into the inlet 251a. The rear panel filter 252 may be coupled to the main body rear panel body 251 at a rear thereof. The main body rear panel 250 may be coupled to the shroud panel 260 at a front of the panel 250. The main body rear panel 250 may be coupled to the base rear panel 210 at a bottom of the panel 250.

In the main body rear panel 250, the indoor heat exchanger 110 may be disposed or provided. The indoor heat exchanger 110 may be provided between the main body rear panel 250 and the shroud panel 260 to allow heat exchange between the air flowing into the inlet 251a of the main body rear panel 250 and a refrigerant. The air may be cooled or heated via the heat exchange with the refrigerant in the indoor heat exchanger 110 and then may be passed to the shroud panel 260. The indoor heat exchanger 110 may be implemented as a combination of a tube and fins. In the tube, the refrigerant may flow. The fins may realize the heat exchange.

The air blowing module 240 may suction air into the inlet 251a of the main body rear panel 250 and discharge the air via the air outlet 290a in the main body front panel 290. When the air blowing module 240 turns on, the air suctioned into the inlet 251a may pass through the Indoor heat exchanger 110 and move through a shroud hole 260a in the shroud panel 260 to the air blowing module 240. Then, the air blowing module 240 may blow the air to move through a guide hole 270a of a guide panel 270 to the outlet 290a of the main body front panel 290.

A plurality of the air blowing module 240 may be provided. In this embodiment, a number of the air blowing module 240 is 2; however, embodiments are not limited thereto. In this embodiment, the two air blowing modules 240 are arranged vertically. The two air blowing modules 240 may correspond to two shroud holes 260a in the shroud panel 260, respectively. The two air blowing modules 240 may be coupled to the guide panel 270 at a rear of the panel 270.

The air blowing module 240 may include an air blower motor 242, an air blower motor bracket 243 to couple the air blower motor 242 to the guide panel 270 at a rear of the panel 270, and an air blowing fan 241 to rotate together with a rotation of the air blower motor 242 to create a flow of air. The air blowing fan 241 may be implemented as a centrifugal fan to receive air axially and then discharge the air radially. The air blowing fan 241 may be configured such that an air suction direction may be oriented toward the shroud hole 260a of the shroud panel 260. After the air is radially discharged from the air blowing fan 241, the air may flow toward a front of the shroud panel 260 and then pass through the guide hole 270a of the guide panel 270. When a plurality of air blowing modules 240 is provided, a plurality of the air blowing fan 241 may be provided. Further, the plurality of the air blowing fans 241 may correspond to the plurality of shroud holes 260a, respectively.

The shroud panel 260 may be configured to guide the air from the inlet 251a in main body rear panel 250 to the air blowing module 240. The shroud panel 260 may define the shroud hole 260a therein, through which the air from the indoor heat exchanger 110 may move to the air blowing module 240. A plurality of the shroud hole 260a may be provided. The plurality of the shroud holes 260a may correspond to the plurality of air blowing modules 240, respectively. In this embodiment, two shroud holes 260a may be vertically arranged to correspond to the two air blowing modules 240 respectively.

A surrounding portion of the shroud hole 260a of the shroud panel 260 may be formed in a dome shape to receive the air blowing module 240 therein. Thus, using the air blowing module 240, the flowing air may be guided to the front thereof.

The shroud panel 260 may be coupled to the connector 230 at a bottom of the panel 260. The shroud panel 260 may be coupled, at a rear thereof, to the main body rear panel 250. The shroud panel 260 may be coupled, at a front thereof, to the guide panel 270.

The guide panel 270 may be configured to guide flowing air using the air blowing module 240 to the outlet 290a. The guide panel 270 may have the guide hole 270a defined therein to guide the air from the air blowing module 240 to the outlet 290a. A plurality of the guide hole 270a may be provided. In this embodiment, two guide holes 270a may be formed at lateral sides relative to a central line C, respectively. Each guide hole 270a may be vertically elongated. Each guide hole 270a may taper from a middle point to bottom and top points, respectively. Each guide hole 270a may be bent toward the central line C at upper and lower portions thereof. The guide hole 270a may be opened or closed by a door 280. Thus, when a plurality of the guide hole 270a is provided, a plurality of doors 280 may be provided.

The guide panel 270 may have the air blowing module 240 mounted thereto at a rear of the panel 270. In this embodiment, two air blowing modules 240 are vertically coupled to the rear portion of the guide panel 270. In a front of the guide panel 270, the door 280 may be provided. In this embodiment, in a front of the guide panel 270, two doors 280 are horizontally arranged.

The guide panel 270 may be at least partially curved such that the door 280 rotates and slides on and along the guide panel 270. In this embodiment, two doors 280 are horizontally arranged, and thus, the guide panel 270 may have a curved front portion at each of lateral sides relative to the vertical central line C. In other words, the curved front portion may be convex toward a front direction to form an arc shape.

The guide panel 270 may be coupled to the shroud panel 260 with the air blowing module 240 being interposed therebetween, thereby to form a single unit. In this embodiment, the guide panel 270, the air blowing module 240, and the shroud panel 260 may be collectively referred to as an air blowing unit or blower 190. That is, the air blowing unit 190 may include the guide panel 270, the air blowing module 240, and the shroud panel 260.

The door 280 may open or close the guide hole 270a and the outlet 290a. The door 280 may be rotatably coupled to the air blowing unit 190. The door 280 may be rotatably coupled to the guide panel 270 or the shroud panel 260 of the air blowing unit 190. In this embodiment, the door 280 is rotatably coupled to the guide panel 270. The door 280 may partially slide on a front surface of the guide panel 270 to open and close the guide hole 270a. Further, the door 280 may partially slide on a rear surface of the main body front panel 290 to open and close the outlet 290a. That is, the door 280 may partially slide between the guide panel 270 and the main body front panel 290 to open and close the guide hole 270a and the outlet 290a concurrently.

The base front panel 220 may form a lower front appearance of the air conditioner. The base front panel 220 may cover the open front of the base rear panel 210 coupled to the connector 230. The base front panel 220 may be implemented as a curved plate. The base front panel 220 may be coupled to the connector 230 at the rear of the base front panel 220, and the base front panel 220 may be coupled to the main body front panel 290 at a top of the base front panel 220.

The main body front panel 290 may form an upper front appearance of the air conditioner. The main body front panel 290 may have the air outlet 290a to discharge the air passing through guide hole 270a using the air blowing module 240. The outlet 290a may correspond to the guide hole 270a in terms of a shape. In this embodiment, the outlets 290a may be two as the two guide holes 270a are defined. The two outlets 290a may be define at both lateral sides relative to the central line C. Each air outlet 290a may be vertically elongated. Each outlet 290a may be bent toward the central line C at upper and lower portions thereof. Each outlet 290a may taper from a middle point to top and bottom points thereof, respectively. The outlet 290a may be opened and closed by the door 280.

The main body front panel 290 may be implemented as a curved plate. The main body front panel 290 may be coupled, at a bottom thereof, to the base front panel 220, and may be coupled, at a side portion thereof, to the main body rear panel 250. The main body front panel 290 may have an input/output hole 290b to partially expose an input/output module 300. The input/output hole 290b may have a circular form.

The input/output module 300 may be configured to receive a user command or display an operation state of the air conditioner. The input/output module 300 may be coupled to the main body front panel 290 at a rear of the panel 290 to be partially exposed through the input/output hole 290b to the outside.

The air conditioner may be applied to the wall-mounted air conditioner, and/or stand-type air conditioner. Hereinafter, for the sake of the convenience, a reference will be made to the wall-mounted air conditioner.

Figure 7:
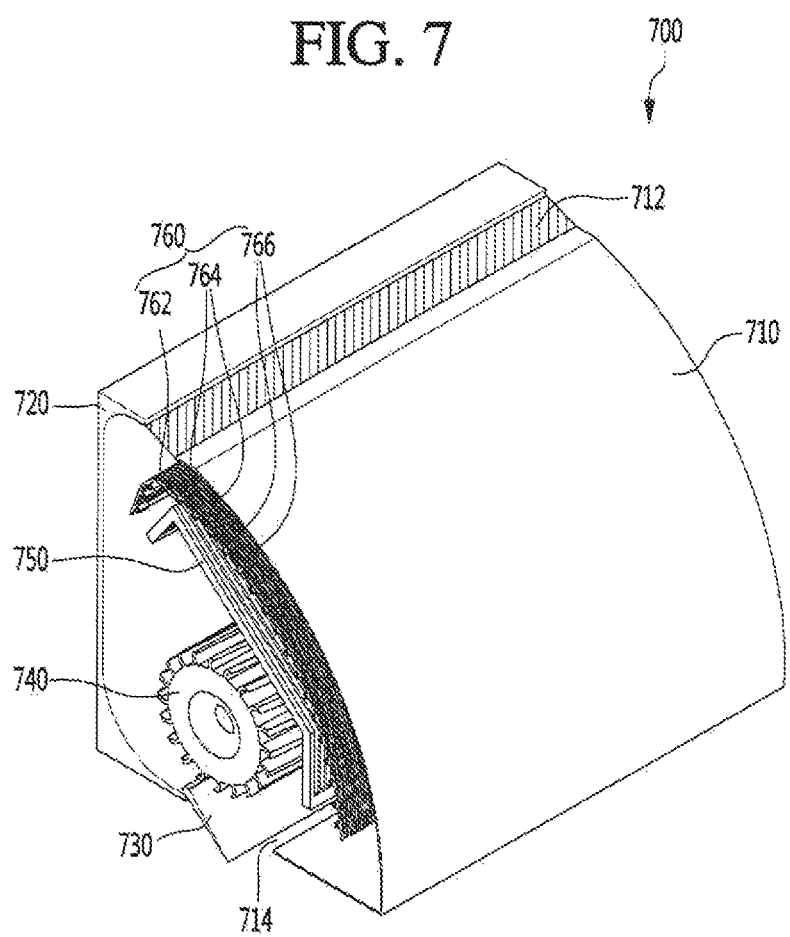
FIG. 7 is a partially cut-away perspective view of an air conditioner according to another embodiment.

FIG. 7 is a partially cut-away perspective view of an air conditioner according to another embodiment. As shown in FIG. 7, the air conditioner in accordance with this embodiment may include a UV sterilization module 760 provided in a main body 700. The UV sterilization module 760 may include a porous main body 762 and a UV lamp 764.

In this embodiment, the main body 700 may include a front panel 710, and a chassis 720. The main body 700 may receive a wind-direction adjustment member or adjuster 730, a fan 740, a heat exchanger 750, the porous main body 762, and the UV lamp 764. As shown in FIG. 7, the air conditioner may include all of the components as described with reference to FIGS. 1 to 4 in addition to the front panel 710, the chassis 720, the wind-direction adjustment member 730, the fan 740, and the heat exchanger 750. With reference to FIG. 7, only the front panel 710, the chassis 720, the wind-direction adjustment member 730, the fan 740, the heat exchanger 750, and the UV sterilization module 760 will be shown and described.

The main body 700 may have an air inlet 712 defined in a top thereof and an air outlet 714 defined in a bottom of thereof. The front panel 710 may define a front portion of the air conditioner. The main body 700 may have the air inlet 712 defined in a top of the air conditioner and the air outlet 714 defined in a bottom of the air conditioner.

The front panel 710 may form a front appearance of the air conditioner, and may be configured to pivot around a top portion thereof to maintain inner components of the air conditioner. Further, in this embodiment, the front panel 710, the chassis 720, the wind-direction adjustment member 730, the fan 740, and the heat exchanger 750 may have the same configurations and functions as described with reference to FIGS. 1 to 4.

In this embodiment, the UV sterilization module 760 may be disposed or provided upstream of the heat exchanger 750 in terms of an air flow path. The UV sterilization module 760 may be disposed or provided in the air suction channel between the front panel 710 and the heat exchanger 750.

The porous main body 762 may be configured to allow passage of air therethrough. The porous main body 762 may have holes 766 formed therein. For example, the porous main body 762 may be implemented as a porous plate having the holes 766 formed therein. Alternatively, the porous main body 762 may be implemented as a mesh of wires wherein the holes 766 may be defined between the wires. Hereinafter, the porous main body 762 may be referred to as a mesh, a web, a main body, a body, a support body, a porous lamp support body, a web main body, a mesh body, or a web body, for example.

The porous main body 762 may have the holes 766 to guide the air to the UV lamp 764. Each hole 766 may have a size larger than or equal to a predetermined size to minimize a channel resistance due to the porous main body 762. Further, the porous main body 762 may be made of an elastic material. The porous main body 762 may have a round surface that conforms to a shape of the heat exchanger 750 or may have at least one curve. The porous main body 762 may be disposed or provided between the main body 700 and the heat exchanger 750.

The UV sterilization module 760 may emit heat using the UV lamp 764. The porous main body 762 may be made of a heat-resistance material. Further, the porous main body 762 may be made of a metal material rather than a plastic material. The porous main body 762 may be made of a material endurable against heat and humidity. For example, the porous main body 762 may be made of aluminum. The aluminum Al may include a pure aluminum and an aluminum alloy.

The porous main body 762 may be disposed or provided upstream of the UV lamp 764 and the heat exchanger 750 in terms of an air flow path. The porous main body 762 may have a photocatalyst coating formed thereon. Thus, the air may be deodorized using the porous main body 762 and then may move to the UV lamp 764 and the heat exchanger 750. That is, when the porous main body 762 has a photocatalyst coating formed thereon, an odorized substance in the air may be minimally or hardly attached to the UV lamp 764. When the odorized substance is attached on the UV lamp 764, the UV lamp 764 may be deteriorated.

For example, the photocatalyst coating may include a $TiO_2$, ZnO, CdS, $ZrO_2$, $V_2O_3$, or $WO_2$ coating. The air that flows into the air inlet 712 may be deodorized using the porous main body 762, and then, may be sterilized using the UV lamp 764. Thus, the deodorized and sterilized air may be passed to the heat exchanger 750.

The porous main body 762 may be configured to allow a minimum air flow interference in the air flow channel. Further, while the air passes through the porous main body 762, the air may flow adjacently to the UV lamp 764. Thus, the air may receive a strong UV intensity. This may lead to improvement in sterilization by the UV sterilization module 760.

The UV sterilization module 760 may include a plurality of the UV lamp 764. Thus, the plurality of UV lamps 764 may be spaced from each other. The plurality of UV lamps 764 may be at least partially arranged in a series manner. The plurality of UV lamps 764 may be entirely arranged in a series manner. The plurality of UV lamps 764 may have a predetermined spacing between them. The plurality of UV lamps 764 may be at least partially arranged in a parallel manner. The plurality of UV lamps 764 may be entirely arranged in a parallel manner.

The plurality of UV lamps 764 may be spaced from the porous main body 762. The plurality of UV lamps 764 may be at least partially disposed or provided between the porous main body 762 and the heat exchanger 750. Further, some of the plurality of UV lamps 764 may be disposed or provided between the porous main body 762 and the heat exchanger 750, while the other of the plurality of UV lamps 764 may be disposed or provided between the porous main body 762 and front panel 710. The UV lamps 764 between the porous main body 762 and front panel 710 may sterilize the air passing between the air inlet 712 and porous main body 762. Subsequently, the UV lamps 764 between the porous main body 762 and the heat exchanger 750 may sterilize the air passing through the porous main body 762.

As described above, the UV lamps may be distributed across the porous main body 762, and the porous main body 762 may have the photocatalyst coating. Thus, the air may be sterilized, a first time, between the air inlet 712 and porous main body 762. Subsequently, the air may be deodorized using the porous main body 762, and then, the air may be sterilized, a second time, between the porous main body 762 and the heat exchanger 750.

The UV sterilization module 760 may include one or more holder (not shown) to support the UV lamp 764. The holder may support the UV lamp 764 such that the UV lamp 764 is spaced from the porous main body 762. A plurality of holders may support the UV lamps 764 respectively. A pair of the holders may support a single UV lamp 764. The UV sterilization module 760 may include a plurality of pairs of the holders. The plurality of pairs of the holders may be spaced from each other.

In one embodiment, the UV sterilization module 760 may include a plurality of UV lamps 764, a power supply (not shown), and an electrical line (not shown). The UV lamp 764 may be implemented as an external electrode type. Therefore, the UV lamp 764 may have a first electrode at one or a first side thereof, and a second electrode at the other or second side thereof. The first electrode and the second electrode may be formed by coating a conductive solder liquid from an outside of the UV lamp 764. Further, the first electrode and second electrode may be formed by coating a silver paste. Furthermore, the first electrode and second electrode may be formed by applying a carbon-nano tube and curing it. That is, the UV lamp 764 and the first electrode and the second electrode may be individually formed. Thus, an electric field may be generated between the first electrode and the second electrode. Then, the electric field may electrically discharge an emission material in the UV lamp 764 to generate UV rays. As the material enclosed in the UV lamp 764 does not contact the first electrode and the second electrode, the UV lamp 764 may have a less amount of heat, to increase a life span of the UV lamp 764.

The power supply may supply power to the UV lamp 764. The power supply may stabilize a current to be supplied to the UV lamp 764. Further, the power supply may generate a high voltage required to generate UV rays in the UV lamp 764. That is, the power supply may be configured to change an output frequency and drive voltage based on a drive frequency and drive voltage for driving the plurality of UV lamps 764. For example, the power supply may act as an inverter, and a stabilizer, for example.

The electric line may connect the power supply and the plurality of UV lamps 764. To be specific, the electric line may connect the first electrode and the second electrode and the power supply. Further, the electric line may realize a parallel connection between the plurality of UV lamps 764 and the power supply. That is, the parallel connection between the power supply and the plurality of UV lamps 764 may allow the plurality of UV lamps 764 to turn on concurrently. Further, when the plurality of UV lamps 764 includes a defective UV lamp, the defective UV lamp may be simply replaced.

Although the UV lamp 764 has been described as an external electrode fluorescent lamp, embodiments are not limited thereto. The electrodes may be disposed or provided within the UV lamp.

Hereinafter, a configuration of the UV lamp 764 will be described. The UV lamp 764 as an external electrode fluorescent lamp may be formed in a hollow bar or tube shape. Further, the UV lamp 764 may have a sealed inner space. The UV lamp 764 may be made of quartz or borosilicate or a glass containing quartz or borosilicate. Further, the UV lamp 764 may have an emission material enclosed therein to generate the UV rays. The emission material may be discharged via an electric field generated between the first electrode and the second electrode at both ends of the UV lamp 764 respectively to generate the UV rays.

For example, the emission material may include at least one of Hg, Ne, Xe, Kr, Ar, XeBr, XeCl, KrBr, KrCl, or $CH_4$. Further, except for Hg, all of the emission materials may be present in a gas state. Further, the emission material may be enclosed in the UV lamp 764 under a constant pressure. For example, the emission material may be enclosed in the UV lamp 764 under an upper or middle pressure. The UV lamp 764 may have a small diameter to facilitate an installation of the lamp in the air conditioner. For example, the UV lamp 764 may have a diameter of about 1 mm to about 7 mm.

When the UV lamp 764 has a diameter below about 1 mm, the lamp may be damaged and filling of the emission material may be not easy. When the UV lamp 764 has a diameter above about 7 mm, air flow resistance due to the lamp may increase. Further, a voltage to discharge the emission material in the UV lamp 764 may increase, thereby increasing power consumption.

The UV lamp 764 may be oriented horizontally in the air conditioner. The UV lamp 764 may be oriented horizontally length-wise. Further, the UV lamp 764 may have a thickness to withstand an inner pressure of the gas enclosed in the UV lamp 764. For example, the UV lamp 764 may have a thickness of about 0.2 mm to about 2 mm. The diameter, length, and thickness of the UV lamp 764 may be not limited to the above dimensions.

The UV lamp 764 may have the first electrode and the second electrode externally disposed or provided at both sides of the UV lamp 764, respectively. Further, the first electrode and the second electrode may be made of a conductive solder liquid at both sides of the UV lamp 764, respectively. Further, the first electrode and the second electrode may be formed by applying a silver paste. Further, the first electrode and the second electrode may be formed by applying and curing a carbon nano-tube (CNT). For example, the UV lamp 764 may be immersed, at both ends thereof, into the conductive solder liquid, and the conductive solder liquid may be cured to form the first electrode and the second electrode.

That is, an outer surface of the UV lamp 764 may dip into the conductive solder liquid, thereby to simplify a manufacturing process thereof. Further, conductive material and conductive solder liquid may include one or more of Ag, carbon nano-tube (CNT), Cu, and Pt. Thus, each of the first electrode and the second electrode may extend from both ends of the UV lamp 764 in a lengthwise direction of the UV lamp 764. Further, each of the first electrode and the second electrode may have a length of at least about 1 cm to about 3 cm from both ends of the UV lamp 764.

When each of the first electrode and the second electrode has a length below about 1 cm, it may be difficult to discharge the emission material in the UV lamp 764. That is, the first electrode and the second electrode may have a small area lowering a discharge efficiency of the emission material. When each of the first electrode and the second electrode has a length above about 3 cm, it may not be difficult to discharge the emission material in the UV lamp 764, but the UV emission area may be smaller due to a smaller area of the first electrode and the second electrode.

The UV sterilization module 760 may sterilize a harmful substance in the air using a parallel connection of the plurality of UV lamps 764 disposed or provided on the porous main body 762, which the air having flowed into the air inlet 712 passes through the porous main body 762 toward the heat exchanger 750. The UV lamp 764 may generate UV rays having a wavelength of about 250 nm to about 260 nm with a strong sterilization against a microorganism. The wavelength of about 250 nm to about 260 nm may have a sterilization effect 1000 to 10000 times larger than a sterilization effect of a near UV.

When the UV ray is irradiated into a DNA of a microorganism, a molecular structure of thymine among bases of the DNA may be intensively destroyed. Thymine absorbing the UV rays may be attached to adjacent thymine or cytosine. Thus, the thymine may be polymerized to stop the replication of DNA. Further, UV rays oxidize phospholipids and proteins forming a cell membrane to suppress life activity of bacteria.

The UV sterilization module 760 may be installed or provided in various locations in the air conditioner. For example, the UV sterilization module 760 may be located between the front panel 710 and the front frame (not shown) of the air conditioner. That is, the porous main body 762 may be coupled to the front panel 710 at a rear of the panel 710 to direct the UV lamp 764 toward the heat exchanger 750.

Further, the UV sterilization module 760 may be located between the front frame and the filter (not shown) of the air conditioner. That is, the porous main body 762 may be coupled to the front frame at a rear of the frame to direct the UV lamp 764 toward the heat exchanger 750.

Further, the UV sterilization module 760 may be located between the filter frame (not shown) and the heat exchanger 750 of the air conditioner. That is, the porous main body 762 may be coupled to the filter frame at a rear thereof to direct the UV lamp 764 toward the heat exchanger 750.

Figure 8:
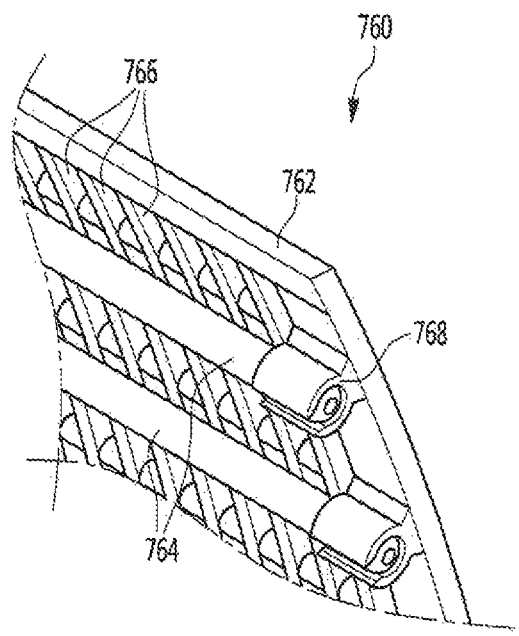
FIG. 8 is a partially enlarged perspective view of a UV sterilization module in the air conditioner according to another embodiment.

FIG. 8 is a partially enlarged perspective view of a UV sterilization module in the air conditioner according to another embodiment. As shown in FIG. 8, the UV sterilization module 760 may include porous main body 762, UV lamp 764, holes 766, and holder(s) 768.

In one embodiment, the UV sterilization module 760 may have holes 766 formed in a polygonal, circular, and/or an elliptical shape. Further, a variation of size of the holes 766 may lead to adjustment of a flow rate of an air passing through the porous main body 762.

The porous main body 762 may have one or more holder 768 at a front thereof. A plurality of the holder 768 may be arranged to be spaced from each other. Further, the porous main body 762 may have a plurality of holders 768 on each of both sides thereof. Each of the plurality of holders 768 may be made of a metal, and may be structured to surround the UV lamp 764.

Further, the porous main body 762 may have holders 768 on one side thereof where the holders 768 may be spaced from each other. The UV lamp 764 may be fitted into the holders 768 at both ends of the UV lamp respectively. Further, the porous main body 762 may have holders 768 arranged at a left, middle, and right points respectively on one side thereof. The UV lamp 764 may be fitted into the holders 768 at the left, middle, and right portions of the UV lamp, respectively.

The porous main body 762 may have a waterproof sealing or seal (not shown) around the holder 768 to prevent corrosion, for example, of the electrodes and holder 768 of the UV lamp 764. Further, although not shown in FIG. 8, the UV sterilization module 760 may include a metal rail (not shown) provided on the porous main body 762. The metal rail may be electrically connected to the holder 768, and thus, current may flow through the metal rail and the holder 768 to the UV lamp 764. The metal rail may be connected to the plurality of holders 768, and thus, the current applied to the metal rail may flow to the plurality of holders 768. The metal rail may act as a parallel connector to realize a parallel connection of the plurality of UV lamps 764.

The metal rail may be referred to as a bus bar.

The plurality of holders 768 may be arranged to be spaced from each other on one surface of the metal rail. That is, the plurality of holders 768 may be arranged on the metal rail at a predetermined distance. A water-proof sealing or seal may be provided to cover not only the electrode, and holder 768 of the UV lamp 764 but also the metal rail.

Figure 9A:
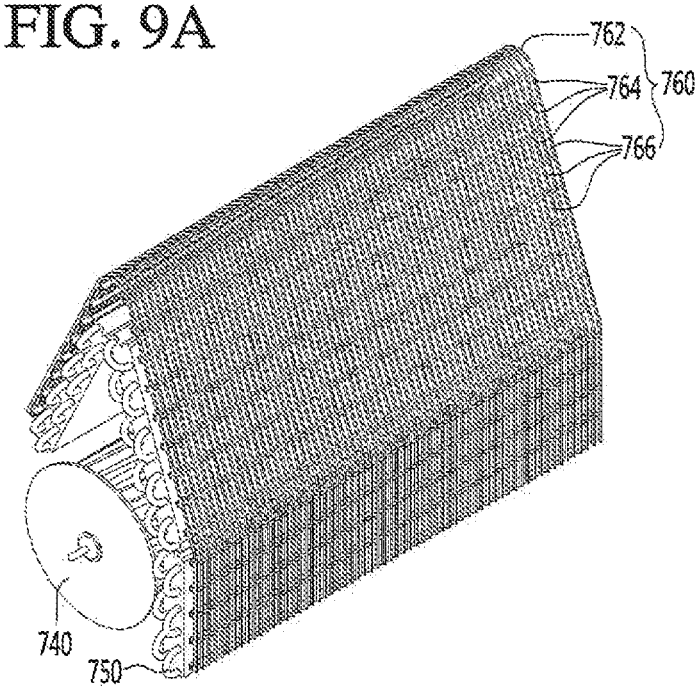
FIGS. 9A-9B are perspective views illustrating positions of a UV sterilization module, a heat exchanger, and a fan in an air conditioner according to an embodiment.
Figure 9B:
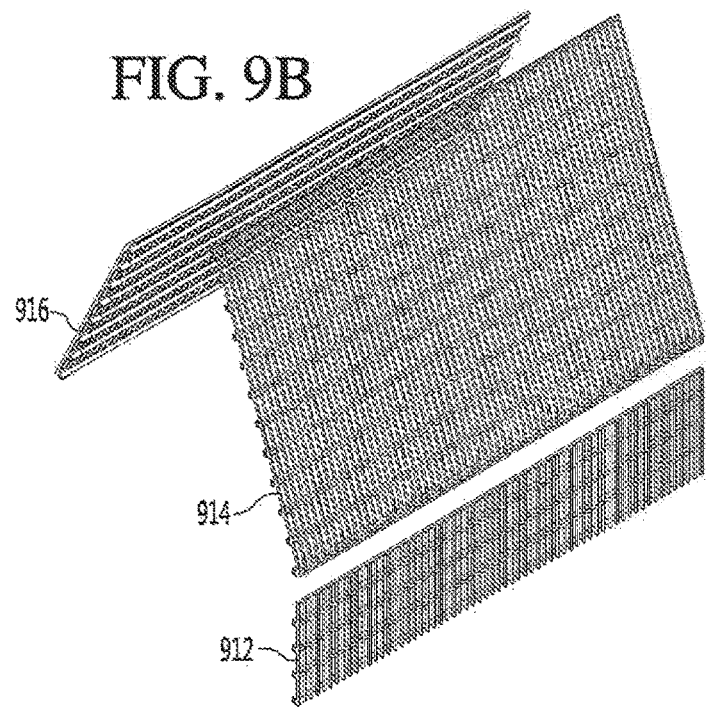

FIGS. 9A-9B are perspective views illustrating positions of a UV sterilization module, a heat exchanger, and a fan in an air conditioner according to an embodiment. As shown in FIGS. 9A-9B, in one embodiment, the air conditioner may include the UV sterilization module 760 including the porous main body 762, the UV lamp 764, the heat exchanger 750, and the fan 740. The UV sterilization module 760 may include the porous main body 762 with holes 766 having a size larger than or equal to a predetermined size so as not to interfere with the air flow.

The UV sterilization module 760 may have the porous main body 762 made of an elastic material. The porous main body 762 may be curved in a conformal manner to a shape of the heat exchanger 750. The UV sterilization module 760 may include a plurality of UV lamps 764. The plurality of UV lamps 764 may be arranged to be spaced from each other on the porous main body 762 in a parallel fashion. The porous main body 762 may include a holder (not shown) to support the UV lamp 764. The UV lamps 764 may be fitted into the holders respectively arranged on the porous main body 762 to be spaced from each other. The UV sterilization module 760 may sterilize a harmful substance in the air using a parallel connection of the plurality of UV lamps 764 disposed or provided on the porous main body 762 while the air having flowed into the air inlet 712 passes through the porous main body 762 toward the heat exchanger 750.

As described above, the porous main body 762 may be made of an elastic material to cover an entire area of the heat exchanger 750. The porous main body 762 may conform to the heat exchanger 750 in shape, and thus, may be coupled to the heat exchanger 750. The porous main body 762 may have a bent portion to realize a conformal registering of the porous main body 762 on the heat exchanger 750. Further, the porous main body 762 may include a first porous main body 912 corresponding to a first or vertical portion of the heat exchanger 750, a second porous main body 914 corresponding to a second or front tilted portion of the heat exchanger 750, and a third porous main body 916 corresponding to a third or rear tilted portion of the heat exchanger 750. Further, although not shown in FIG. 9, in one embodiment, the porous main body of the UV sterilization module 760 may vary in a size and shape depending on a size and shape of the UV lamp.

Figure 10A:
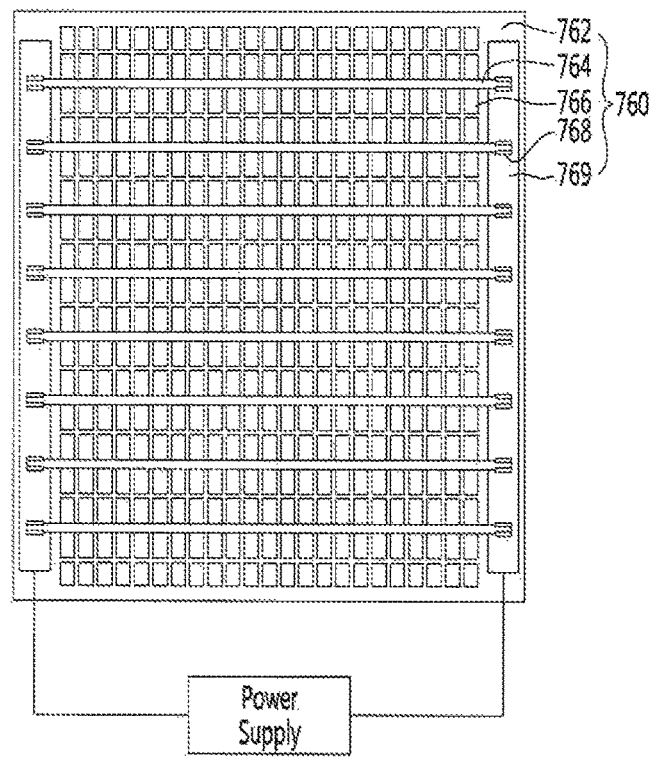
FIGS. 10A-10B show an example of a UV sterilization module according to an embodiment having metal rails.
Figure 10B:
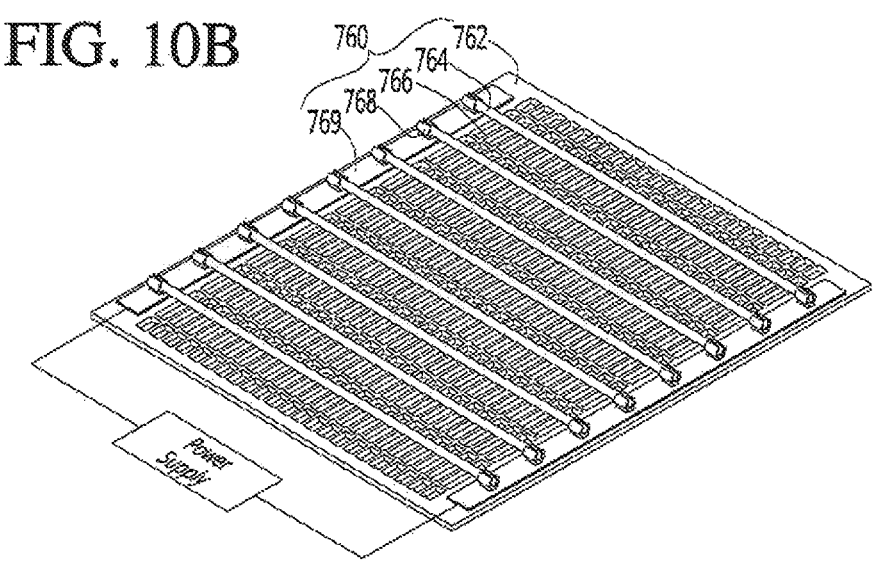

FIGS. 10A-10B show an example of a UV sterilization module according to an embodiment having metal rails. As shown in FIGS. 10A-10B, in one embodiment, the UV sterilization module 760 may include porous main body 762, a plurality of UV lamps 764, a plurality of holes 766, a plurality of holders 768, and metal rails 769.

The porous main body 762 may have the plurality of holes 766 to receive air. The air into the plurality of holes 766 may be sterilized using the plurality of UV lamps 764. The metal rails 769 may be provided at first and second or left and right sides of the porous main body 762, respectively, with a given length. The plurality of holders 768 may be arranged to be spaced from each other on the metal rails 769. Thus, the plurality of holders 768 may be disposed or provided on first and second or left and right portions of the porous main body 762. Each of the plurality of UV lamps 764 may be fitted or provided with a pair of holders at the left and right portions of the porous main body, respectively.

In one embodiment, the UV sterilization module 760 may receive power from a power supply. Each UV lamp 764 may receive power via the electric line. Further, the holder 768 may be made of a metal, and the holder 768 may be connected to the electric line to supply power to each UV lamp. Further, employing the plurality of UV lamps 764 as the external electrode UV lamp may allow an easy power supply. That is, when the plurality of metal holders 768 and metal rails 769 are disposed and both metal rails 769 receive the power, all UV lamps 764 may receive the power concurrently. In this way, using the metal rails, UV lamp mounting and power supply may be facilitated.

Figure 11A:
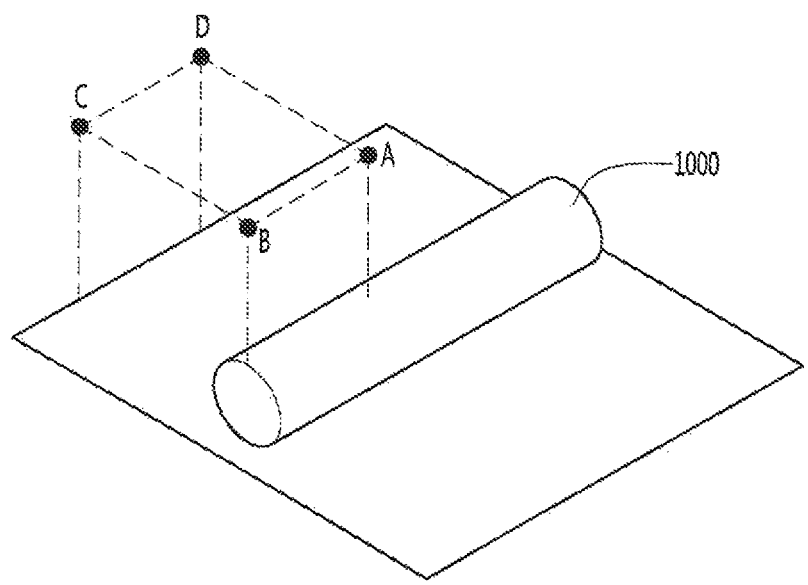
FIGS. 11A-11B are diagrams for describing power energies measured in a given region when a single related art UV lamp is employed.
Figure 11B:
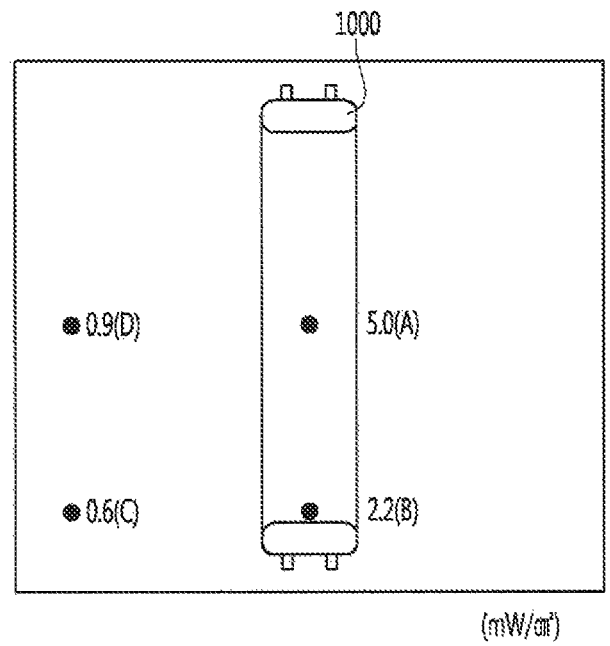
Figure 12A:
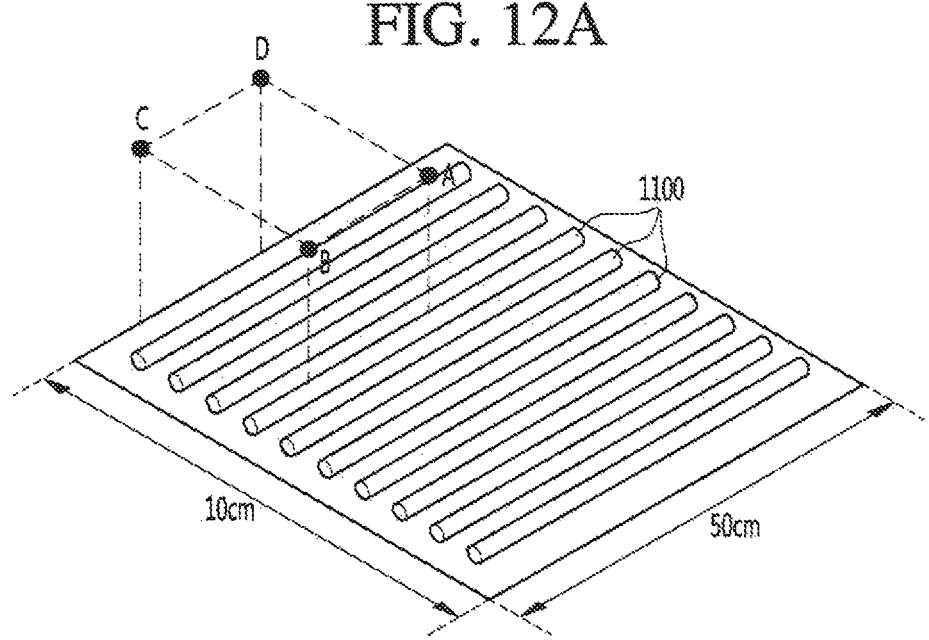
FIGS. 12A-12B are diagrams for describing power energies measured in a given region when a parallel combination of multiple UV lamps according to an embodiment is employed.
Figure 12B:
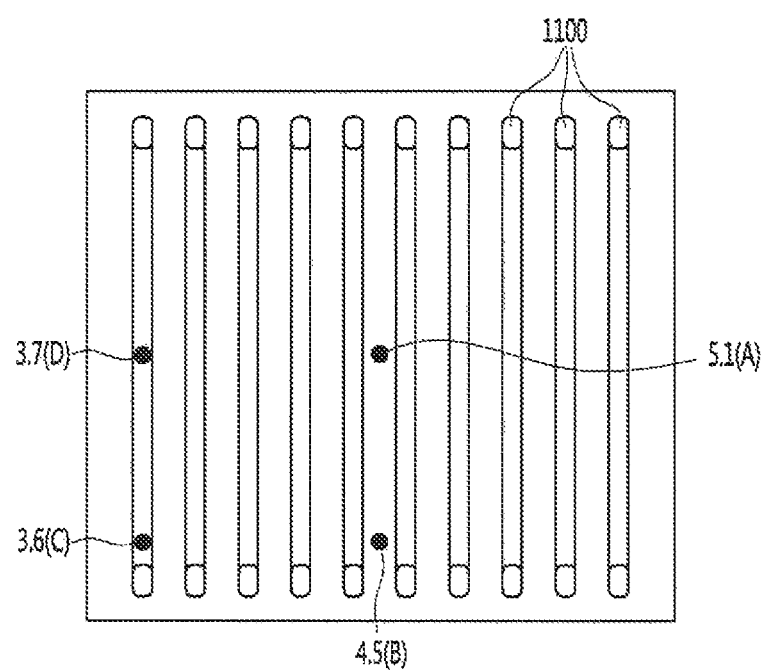

FIGS. 11A-11B are diagrams for describing power energies measured in a given region when a single conventional UV lamp is employed. FIGS. 12A-12B are diagram for describing power energies measured in a given region when a parallel combination of multiple UV lamps according to an embodiment is employed.

In FIGS. 11A-11B, a single related art UV lamp 1000 may be used to conduct UV sterilization, while in FIGS. 12A-12B, in one embodiment, a parallel connection of ten UV lamps 1100 may be used to conduct UV sterilization.

As shown in FIGS. 11A-11B, when the single related art UV lamp 1000 or is employed works, power energy measured in an A region amounts to about 5 m W/cm$^2$; power energy measured in a B region amounts to about 2.2 mW/cm$^2$; power energy measured in a C region amounts to about 0.6 mW/cm$^2$; and power energy measured in a D region amounts to about 0.9 mW/cm$^2$. As shown in FIGS. 12A-12B, in the one embodiment, when the ten UV lamps 1100 work, or are employed power energy measured in an A region amounts to about 5.1 W/cm$^2$; power energy measured in a B region amounts to about 4.5 mW/cm$^2$; power energy measured in a C region amounts to about 3.6 mW/cm$^2$; and power energy measured in a D region amounts to about 3.7 mW/cm$^2$.

That is, in the one embodiment, a plurality of the UV lamps 1100 with small diameters respectively works concurrently, a high power density may be achieved due to a small spacing between the lamps, and thus, an overlapping effect may occur. In contrast, a lower power density may be achieved due to a larger spacing between the lamps, and thus, a reduced overlapping effect may occur.

Thus, an approach where the single related art UV lamp 1000 works may have a larger power consumption than the present approach where the present ten UV lamps 1100 work concurrently. Therefore, taking into account power consumption, a space efficiency, and UV sterilization, using the plurality of the UV lamps 1100 in the one embodiment may be more effective than using the single related art UV lamp.

Figure 13:
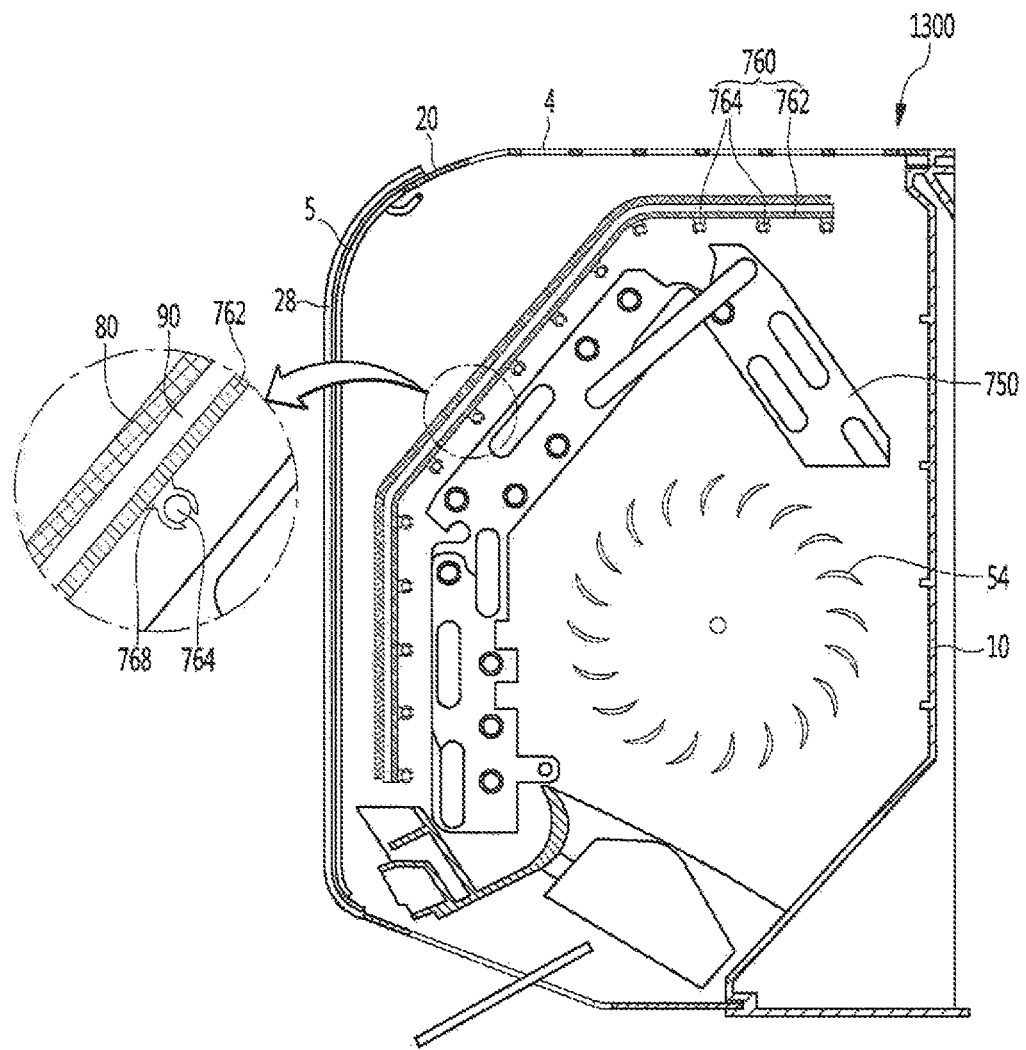
FIGS. 13 to 15 illustrate an embodiment of an air conditioner including a UV sterilization module.
Figure 14:
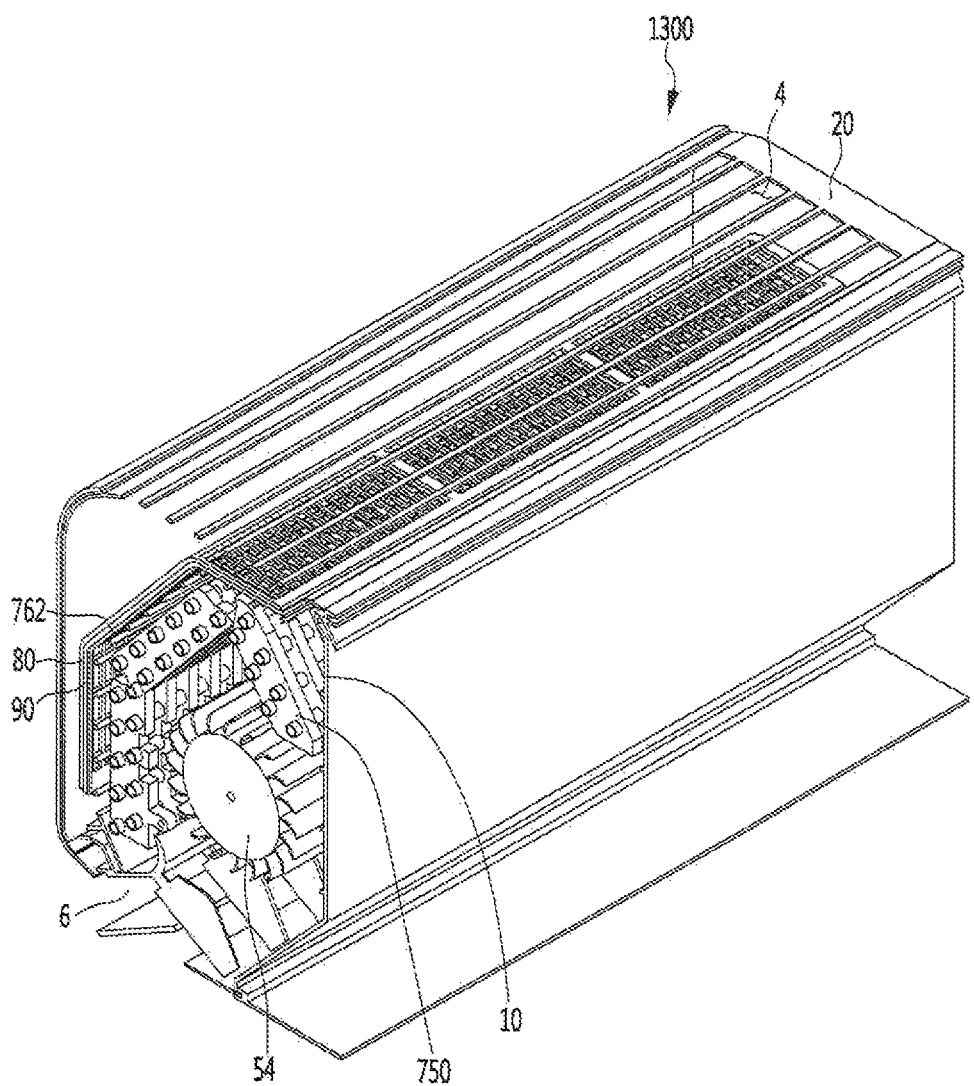
Figure 15:
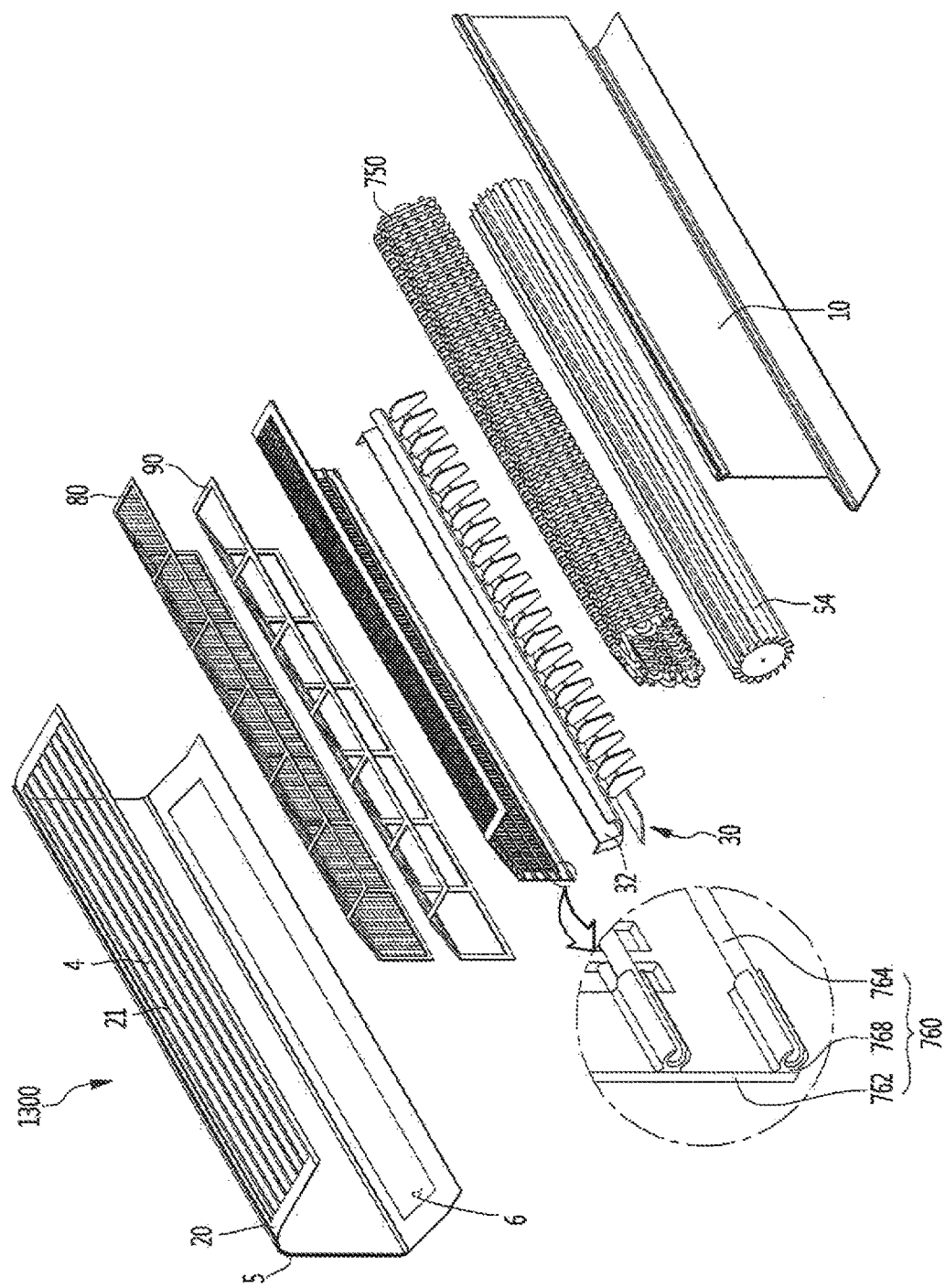

FIGS. 13 to 15 illustrate an embodiment of an air conditioner including a UV sterilization module. As shown in FIGS. 13 to 15, in one embodiment, the main body 1300 of the air conditioner may receive therein heat exchanger 750 and filter frame 90. Further, UV sterilization module 760 may be disposed or provided between the heat exchanger 750 and the filter frame 90.

The filter frame 90 may be spaced from the heat exchanger 750 in an air flow direction. Between them, there may be defined a gap in which the UV sterilization module 760 may be disposed or provided to be spaced from the heat exchanger 750. This gap may be larger than an air flow direction thickness of the UV sterilization module 760. While the UV sterilization module 760 is spaced from the heat exchanger 750, the UV sterilization module 760 may generate UV rays.

The porous main body 762 of the UV sterilization module 760 may be disposed or provided between the heat exchanger 750 and the filter frame 90. The porous main body 762 may face the heat exchanger 750.

The UV sterilization module 760 may include the holder 768 on the porous main body 762 to support the UV lamp 764. The holder 768 may be mounted to the porous main body 762 such that the holder 768 may protrude from a surface of the porous main body 762 facing the heat exchanger 750. Each UV lamp 764 may be mounted to the holder 768 of the porous main body 762. Each UV lamp 764 may be spaced from the porous main body 762 via the holder 768. Each UV lamp 764 may be spaced from the porous main body 762 in an air flow direction. The UV lamp 764 may generate UV rays in the air flow direction between the porous main body 762 and the heat exchanger 750. The porous main body 762 may not have the holder 768 on a surface opposite to the surface facing the heat exchanger 750. The porous main body 762 may be coupled to the filter frame 90. The filter frame 90 may have a coupler (not shown) to which the porous main body 762 may be detachably coupled.

The porous main body 762 may be coupled to the filter frame 90 at the surface opposite to the surface of the body 762 facing the heat exchanger 750. The plurality of UV lamps 764 on the surface of the porous main body 762 facing the heat exchanger 750 may emit the UV rays toward the heat exchanger 750.

The air suctioned into the air inlet 4 may pass through the filter 80, the filter frame 90, and the porous main body 762 sequentially and may move to the heat exchanger 750. In this way, the UV lamp 764 may emit the UV rays to sterilize the air.

The porous main body 762 may have a length equal to or larger than a length of the heat exchanger 750. In contrast, the UV lamp 764 may have a width smaller than or equal to a width of the heat exchanger 750. A spacing between the porous main body 762 and the heat exchanger 750 may be set to an optimal distance based on experimental data. Further, the UV sterilization module 760 may include a plurality of UV lamps 764. The plurality of UV lamps 764 may be individually or collectively controlled based on a user input.

Figure 16:
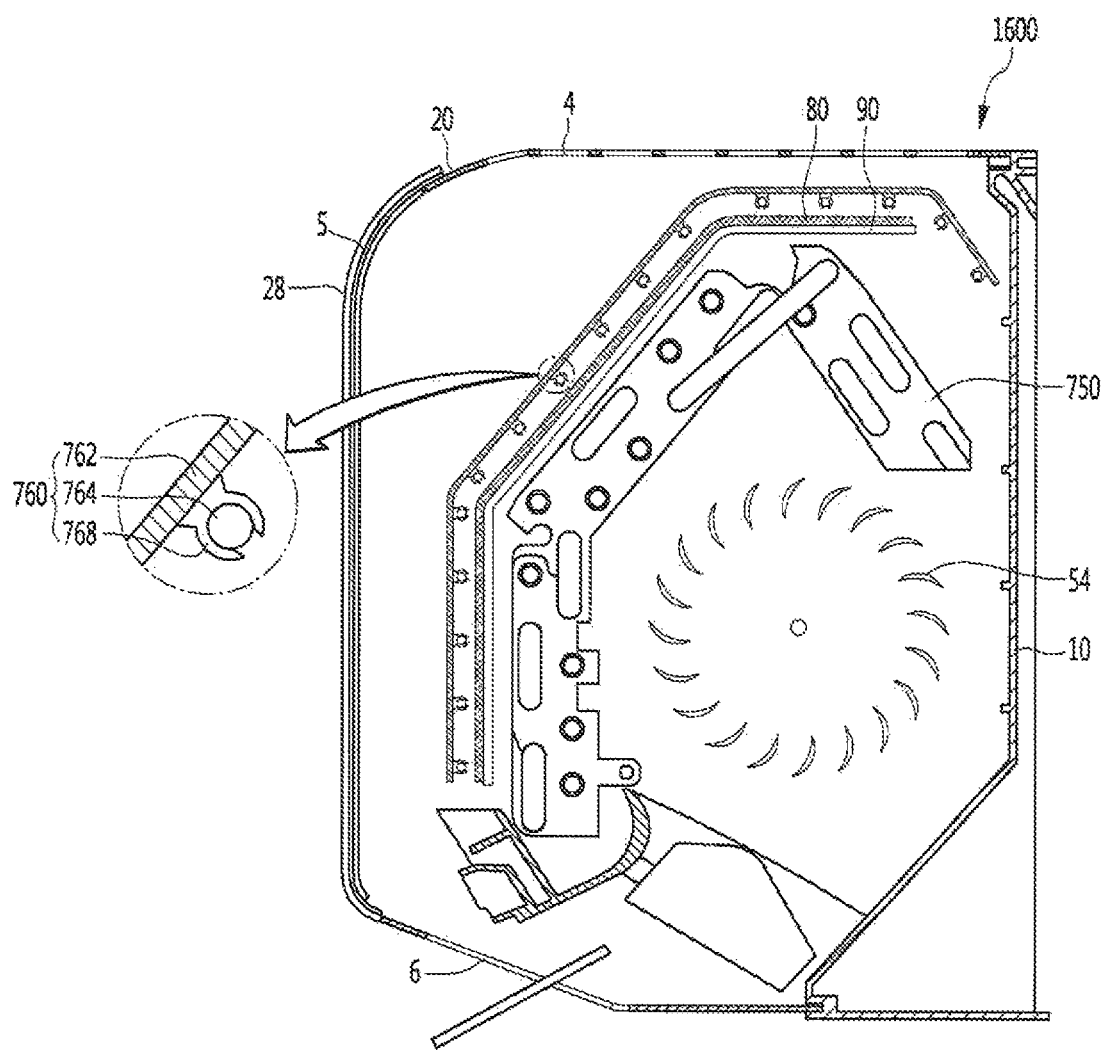
FIGS. 16 to 18 illustrate another embodiment of an air conditioner including a UV sterilization module.
Figure 17:
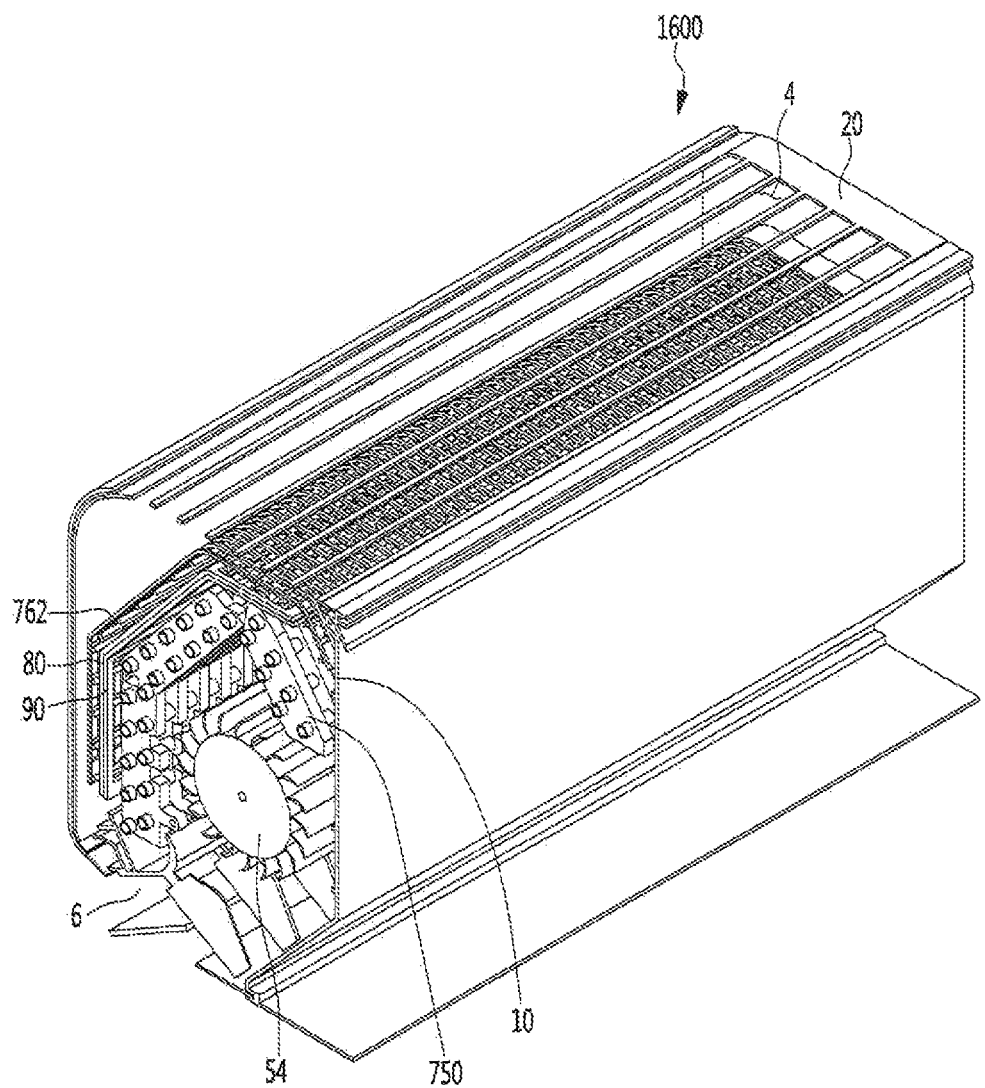
Figure 18:
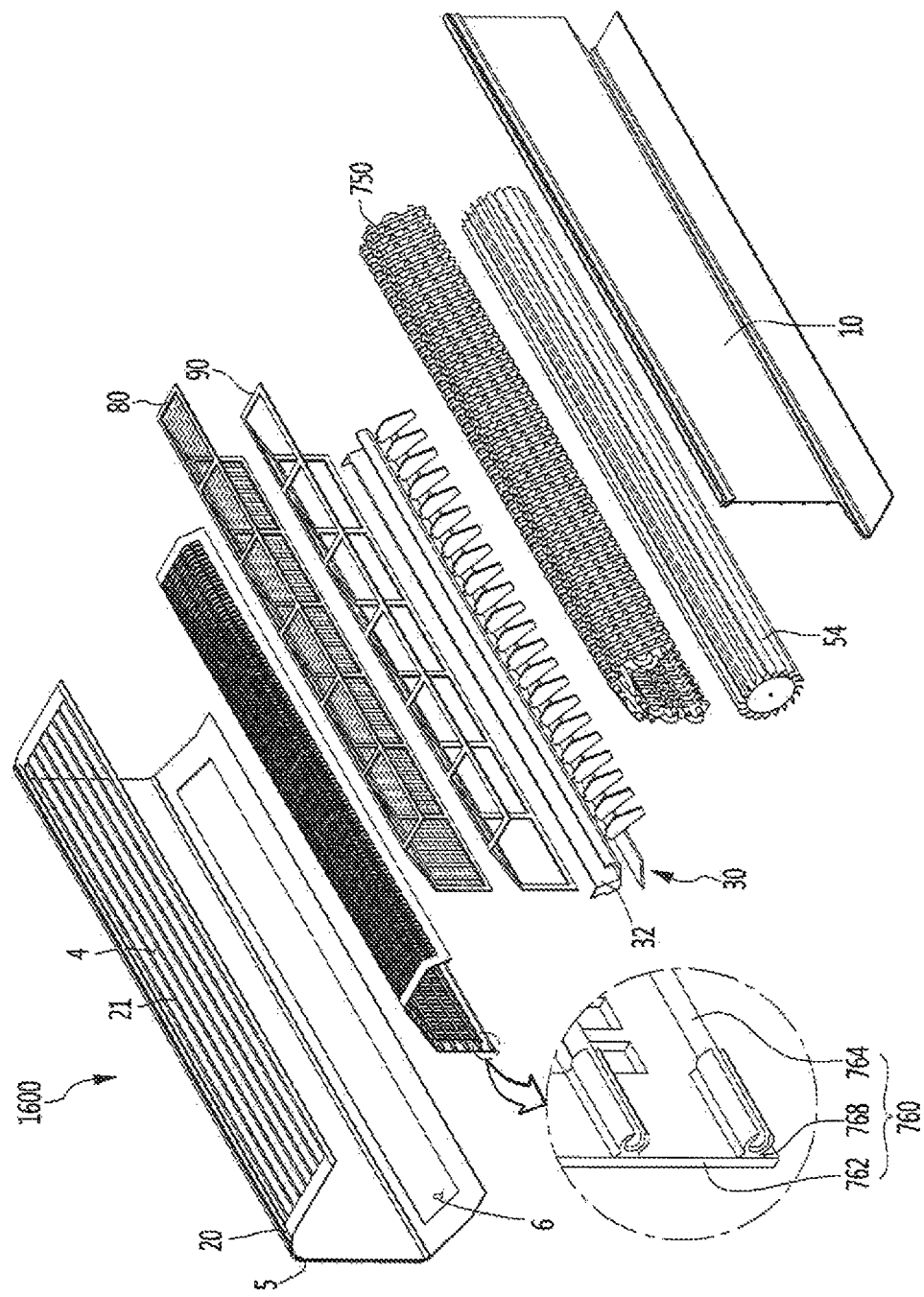

FIGS. 16 to 18 illustrate another embodiment of an air conditioner including a UV sterilization module. As shown in FIGS. 16 to 18, in one embodiment, the UV sterilization module 760 may be disposed or provided between the air inlet 4 and the filter 80.

In this embodiment, the UV sterilization module 760 may have the holder 768 protruding from a surface of the porous main body 762 facing the filter 80. The holder 768 may support the UV lamp 764. Each UV lamp 764 may be spaced from the porous main body 762 via the holder 768. In this embodiment, the holder 768 may not be positioned on a front of the porous main body 762. The porous main body 762 may have a porous main body coupler (not shown) on a surface opposite to a surface thereof facing the filter 80. The porous main body coupler may be coupled to at least one of the front frame 20 or chassis 10.

The porous main body 762 may have a curved surface or may have at least one bent portion. The porous main body 762 may have a first region facing the front frame 20. The porous main body 762 may have a second region facing the chassis 10. The porous main body coupler may be formed on or in one of the first region or the second region. Further, the porous main body coupler may be formed on or in each of the first region or the second region.

The porous main body 762 may be coupled via the coupler to the front frame 20 and the chassis 10 at a surface opposite to the surface of the porous main body 762 facing the filter 80. In this way, the parallel combination of the plurality of UV lamps 764 between the porous main body 762 and the filter 80 may emit the UV rays toward the filter 80.

The air suctioned into the air inlet 4 may pass through the porous main body 762, between the plurality of UV lamps 764, to the filter 80 and the filter frame 90 in this order and then move to the heat exchanger 750. In this way, the UV rays from the UV lamp 764 may sterilize the air passing between the UV lamps 764, the air passing through the filter 80, and the air passing through the heat exchanger 750.

The porous main body 762 may have a length equal to or larger than a length of the heat exchanger 750. In contrast, the UV lamp 764 may have a width smaller than or equal to a width of the heat exchanger 750. A spacing between the porous main body 762 and the heat exchanger 750 may be set to an optimal distance based on experimental data. Further, the UV sterilization module 760 may include a plurality of UV lamps 764. The plurality of UV lamps 764 may be individually or collectively controlled based on a user input.

In one embodiment, an air conditioner may include main body 1600 having air inlet 4 and air outlet 6 defined therein; filter 80 received in the main body 1600 to filter air; heat exchanger 750 configured to perform heat exchange between a refrigerant and the air suctioned into the main body 1600; and UV sterilization module 760 configured to sterilize the air suctioned into the main body 1600. The UV sterilization module 760 may include porous main body 762 in a mesh form, and a plurality of UV lamps 764. The porous main body 762 may include a bent portion to allow the porous main body to conform to a shape of the heat exchanger 750. The main body 1600 may include chassis 10, and front frame 20 in front of the chassis 10. An inner space may be defined between the chassis 10 and the front frame 20. The porous main body 762 may be coupled to at least one of the chassis 10 or the front frame 20. The plurality of UV lamps 764 may be arranged to be spaced from each other between the air inlet 4 and the heat exchanger 750.

In one embodiment, an air conditioner may include main body 1600 having air inlet 4 and air outlet 6 defined therein; filter 80 received in the main body 1600 to filter air; heat exchanger 750 configured to perform heat exchange between a refrigerant and the air suctioned into the main body 1600. The heat exchanger 750 may have first and second surfaces with different planes. The air conditioner may further include mesh member 762 having a first surface that conforms in shape to the first surface of the heat exchanger 750, and a second surface that conforms in shape to the second surface of the heat exchanger 750; and a plurality of UV lamps 764 supported on the mesh member.

Further, in one embodiment, the air conditioner may include rear frame 10, front frame 20, air inlet 4 between the rear frame 10 and the front frame 20, heat exchanger 750 to lower a temperature of the air suctioned into the air inlet 4, frame porous lamp support body 762 defined as a plane on the front frame 20 and the rear frame 10 to have a two dimensional bending, a plurality of UV lamps 764 provided on at least one surface of the porous lamp support body 762 to irradiate the UV rays toward the heat exchanger 750.

Further, in one embodiment, the air conditioner may include front frame 20 defining a front of the air conditioner; rear frame 10 defining a rear of the air conditioner; air inlet 4 defined between an upper portion of the front frame 20 and an upper portion of the rear frame 10; filter 80; heat exchanger 750 disposed or provided adjacent to a surface of the filter facing the rear frame 10; web main body 762 in a mesh form coupled to the front frame 20 and the rear frame 10 at inner sides thereof; a plurality of couplers 768 disposed or provided at left, middle, and right (first, second, and third) portions of the web main body 762, respectively; a plurality of UV lamps 764 mounted to the plurality of couplers, respectively; fan 54 to blow air entering into the air inlet 4; and air outlet 6 defined between a lower portion of the front frame 20 and a lower portion of the rear frame 10.

Further, in one embodiment, the air conditioner may include main body 1600 having air inlet 4 and air outlet 6 defined therein; filter 80 received in the main body 160 to filter air; heat exchanger 750 configured to perform a heat exchange between a refrigerant and the air suctioned into the main body 1600; web mesh body 762 to allow air passage therethrough; a metal rail provided on the web body 762 and having couplers thereon; and a plurality of UV lamps 764 coupled to the couplers on the metal rail.

Further, in one embodiment, the air conditioner may include main body 1600 having air inlet 4 and air outlet 6 defined therein; filter 80 received in the main body 160 to filter air; heat exchanger 750 configured to perform a heat exchange between a refrigerant and the air suctioned into the main body; and UV sterilization module 760 to sterilize the air in the main body 1600. The UV sterilization module 760 may include porous main body 762 and a plurality of UV lamps 764. The plurality of UV lamps 764 may be arranged to be spaced from each other in a parallel manner between the air inlet 4 and the heat exchanger 750. The porous main body 762 may have a horizontal width smaller than a horizontal width of the heat exchanger 750.

Figure 19:
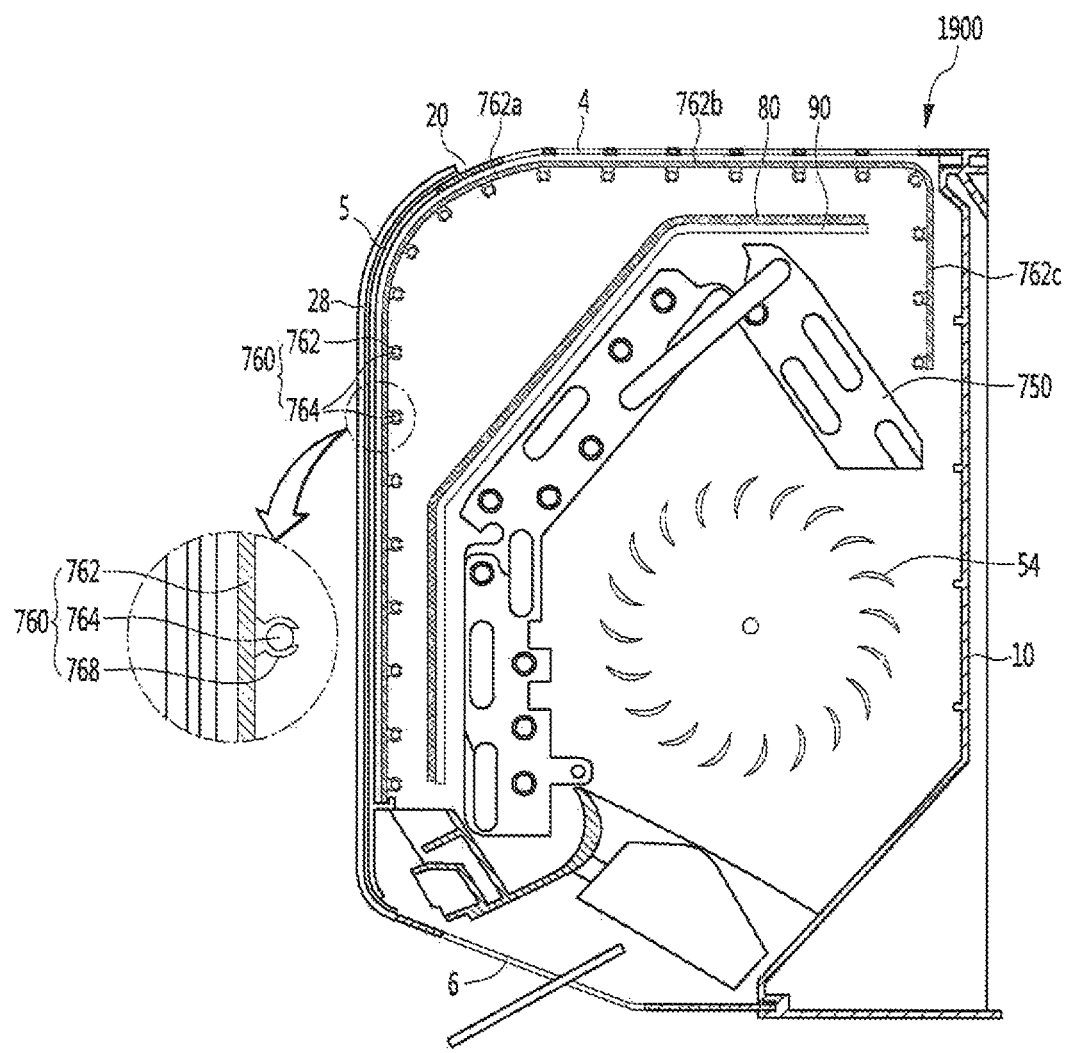
FIGS. 19 to 21 illustrate yet another embodiment of an air conditioner including a UV sterilization module.
Figure 20:
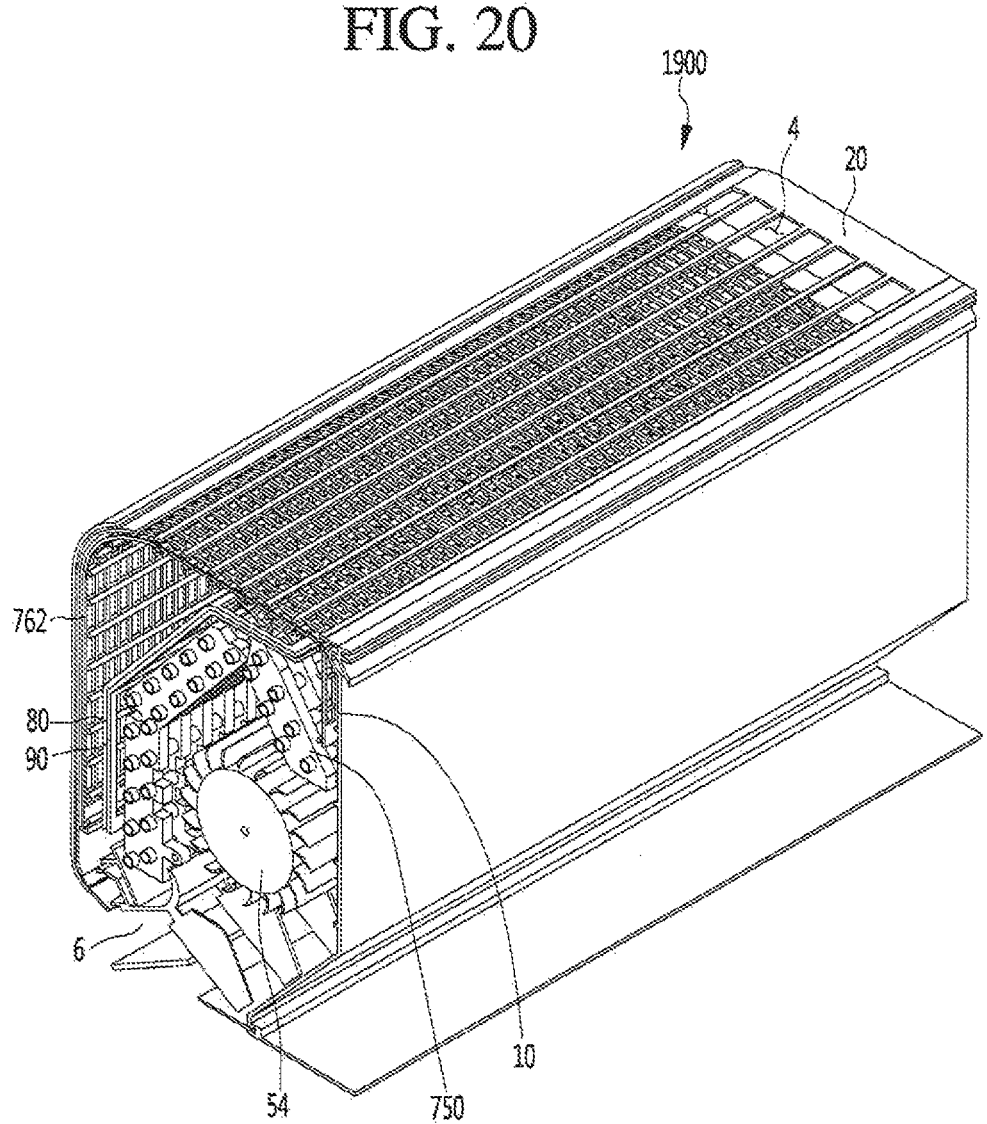
Figure 21:
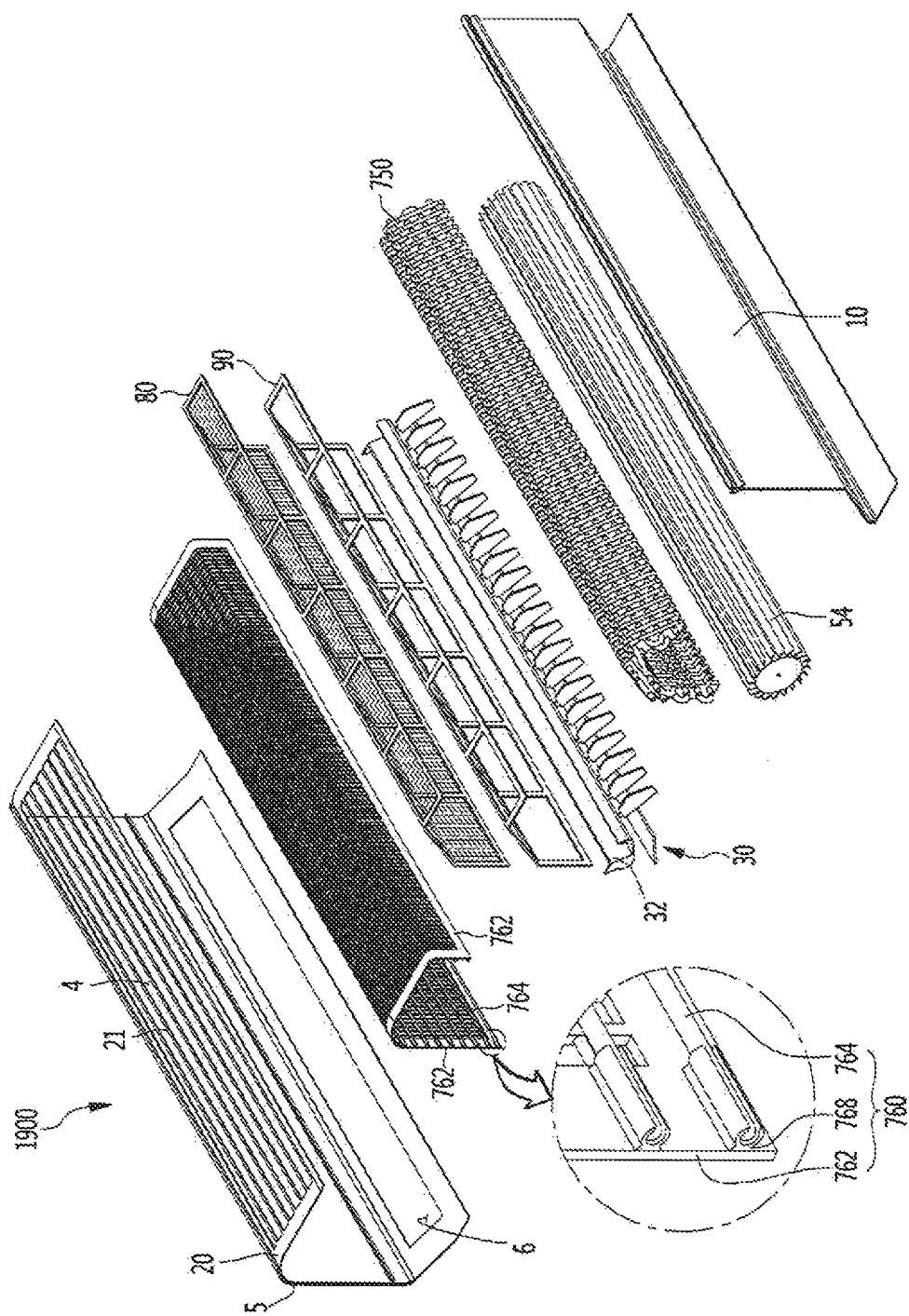

FIGS. 19 to 21 illustrate yet another embodiment of an air conditioner including a UV sterilization module. As shown in FIGS. 19 to 21, in one embodiment, the air conditioner may include UV sterilization module 760 between front frame 20 and filter 80.

In this embodiment, the UV sterilization module 760 may have holders 768 disposed or provided on a surface of the porous main body 762 facing the filter 80 to support the UV lamp 764. Further, each UV lamp 764 may be mounted to the holder 768 to be spaced from the porous main body 762. In this embodiment, the holder 768 may not be present on a front of the porous main body 762. The porous main body 762 may have porous main body couplers (not shown) on a surface thereof opposite to a surface facing the filter 80 to be coupled to at least one of the front frame 20 or the chassis 10. The porous main body 762 may be curved or have at least one bent portion.

The porous main body 762 may have a first region to facing the front frame 20. The porous main body 762 may have a second region facing the chassis 10. The porous main body coupler may be formed on one of the first region or the second region. Further, the porous main body coupler may be formed on each of the first region or the second region.

The porous main body 762 may include a front body 762a facing an inner surface of the front frame 20 and an upper body 762b that extends from the front body and facing the air inlet 4. The porous main body 762 may further include a rear body 762c that extends downwards from the upper body 762b and faces the chassis 10. The rear body 762c may be at least partially disposed or provided between the heat exchanger 750 and chassis 10.

The porous main body 762 may be coupled via the coupler to the front frame 20 and the chassis 10 on a surface opposite to a surface facing the filter 80. As a result, the plurality of UV lamps 764 may be arranged between the porous main body 762 and the filter 80 in a parallel manner to generate the UV rays toward the filter 80.

The air suctioned into the air inlet 4 may pass through the porous main body 762, between the plurality of UV lamps 764, and then, may pass through the filter 80 and the filter frame 90 in this order and then move to the heat exchanger 750. In this way, the UV rays from the UV lamp 764 may sterilize the air passing between the UV lamps 764, the air passing through the filter 80, and the air passing through the heat exchanger 750.

The porous main body 762 may have a length equal to or larger than a length of the heat exchanger 750. In contrast, the UV lamp 764 may have a width smaller than or equal to a width of the heat exchanger 750. A spacing between the porous main body 762 and the heat exchanger 750 may be set to an optimal distance based on experimental data. Further, the UV sterilization module 760 may include a plurality of UV lamps 764. The plurality of UV lamps 764 may be individually or collectively controlled based on a user input.

Figure 22:
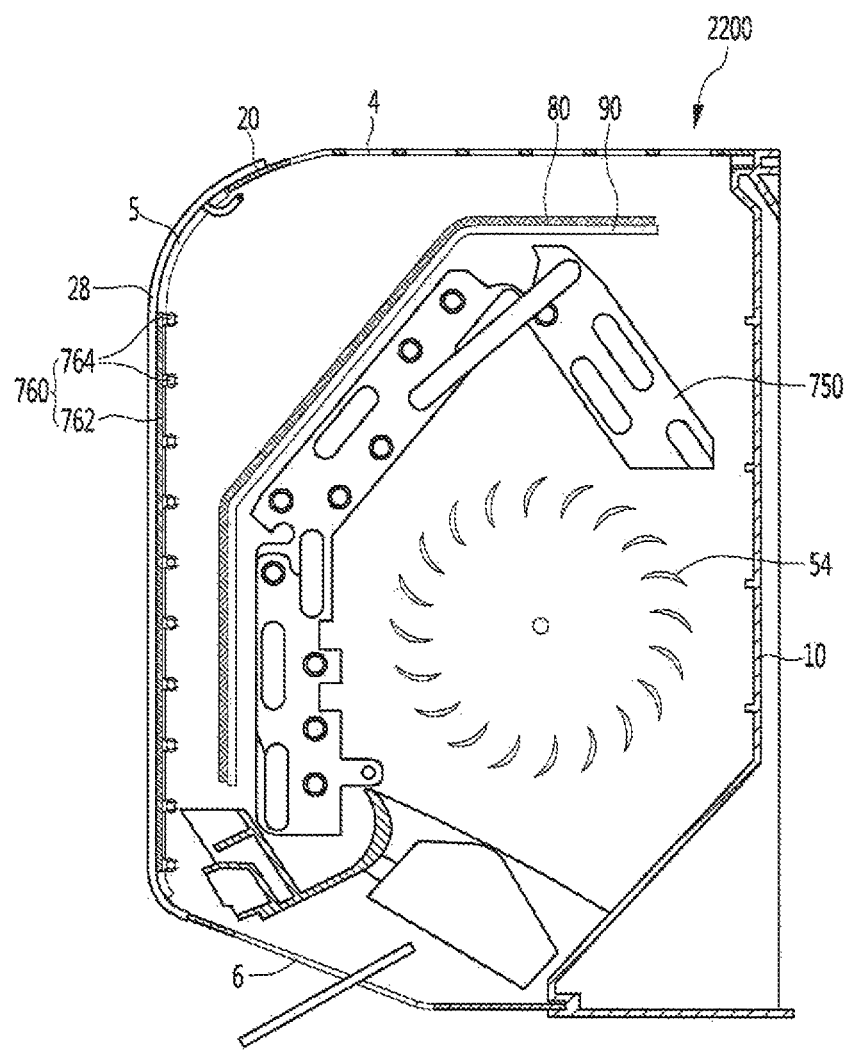
FIGS. 22 to 24 illustrate still another embodiment of an air conditioner including a UV sterilization module.
Figure 23:
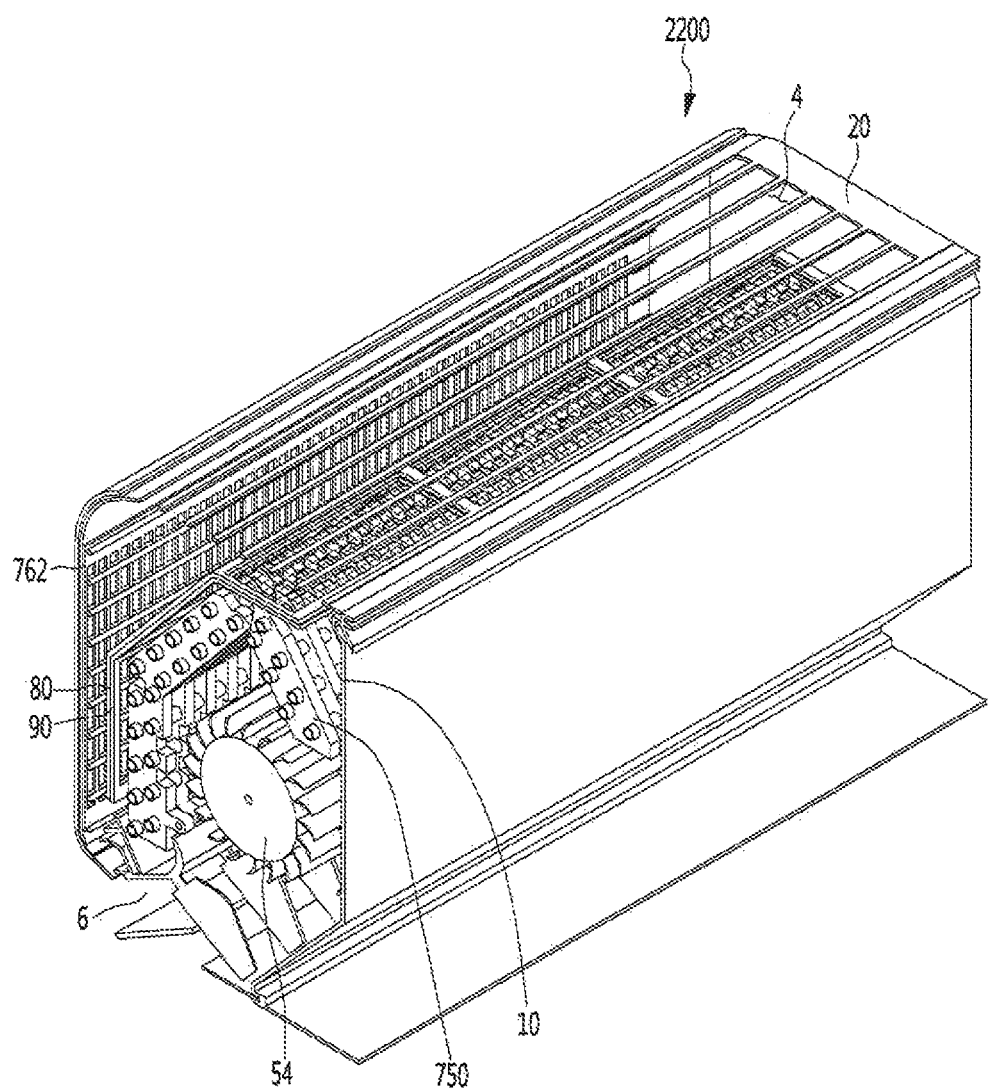
Figure 24:
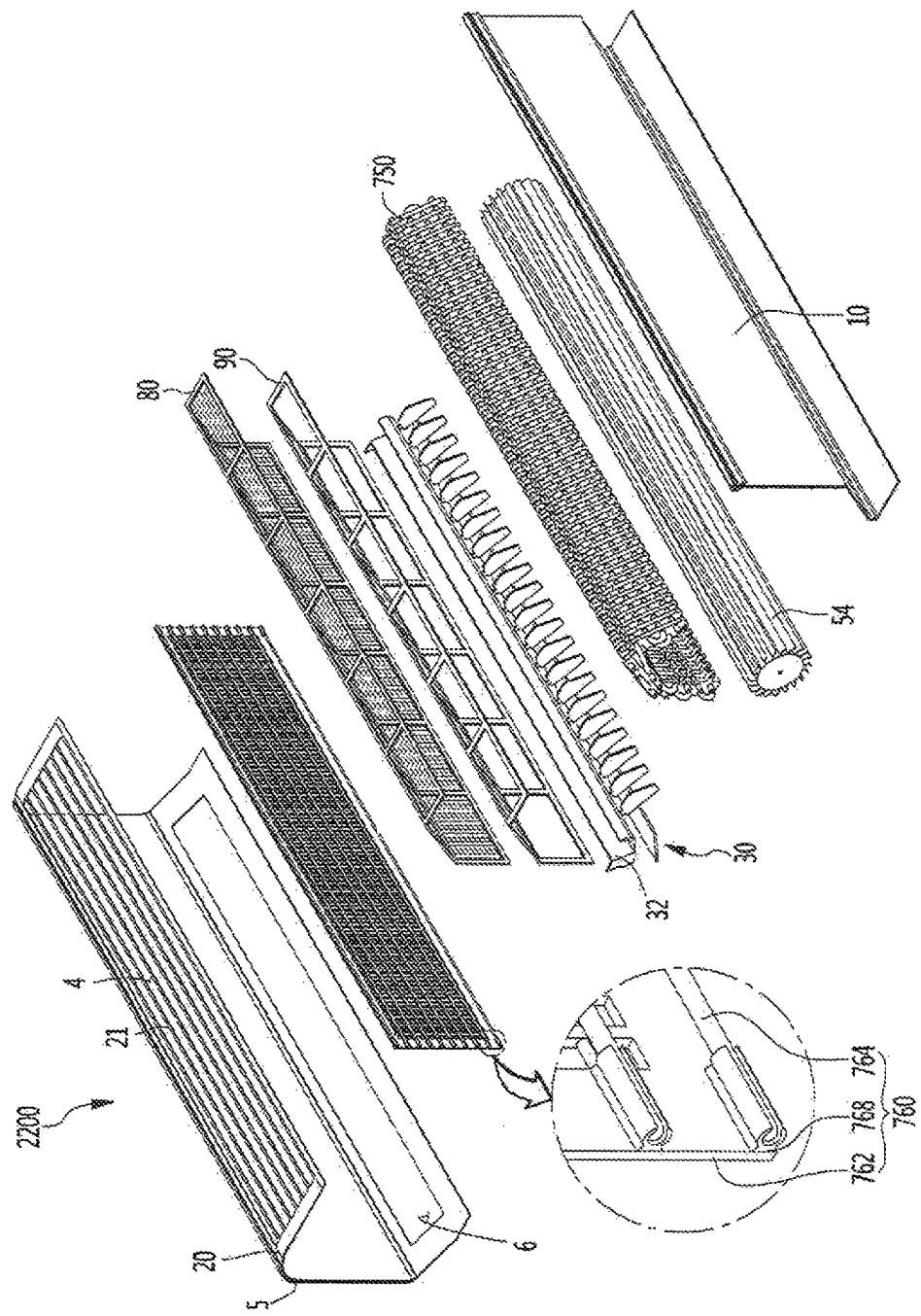

FIGS. 22 to 24 illustrate still another embodiment of an air conditioner including a UV sterilization module. As shown in FIGS. 22 to 24, in one embodiment, the air conditioner may have a front panel 28 defining a front of main body 2200. Further, UV sterilization module 760 may be disposed or provided between the front panel 28 and filter 80 to emit the UV rays.

The UV sterilization module 760 may have holders provided on a surface of porous main body 762 facing the filter 80. Further, each UV lamp 764 may be coupled to each holder to be spaced from the porous main body 762, the front panel 28, the filter 80, and the heat exchanger 750.

The porous main body 762 may have a front facing the front panel 28. The holders may not be present on the front of the porous main body 762. The porous main body 762 may have couplers (not shown) on a front surface to be coupled to the front panel 28.

The porous main body 762 may be coupled via the coupler to the front panel 28 at the front of the body 762. Thus, the plurality of UV lamps 764 disposed or provided on a rear of the porous main body 762 in a parallel manner may emit the UV rays to the filter 80.

The air suctioned into the air inlet 4 may pass through the filter 80 and the filter frame 90 in this order and to the heat exchanger 750. In this way, the UV lamp 764 may emit the UV rays toward the filter 80 and the heat exchanger 750 at the front of the filter 80 and the heat exchanger 750. Further, the air entering into the air inlet 4 may pass through the filter 80 and the heat exchanger 750 such that the air may be sterilized using the UV rays. Further, the UV sterilization module 760 may include a plurality of UV lamps 764. The plurality of UV lamps 764 may be individually or collectively controlled based on a user input.

Figure 25:
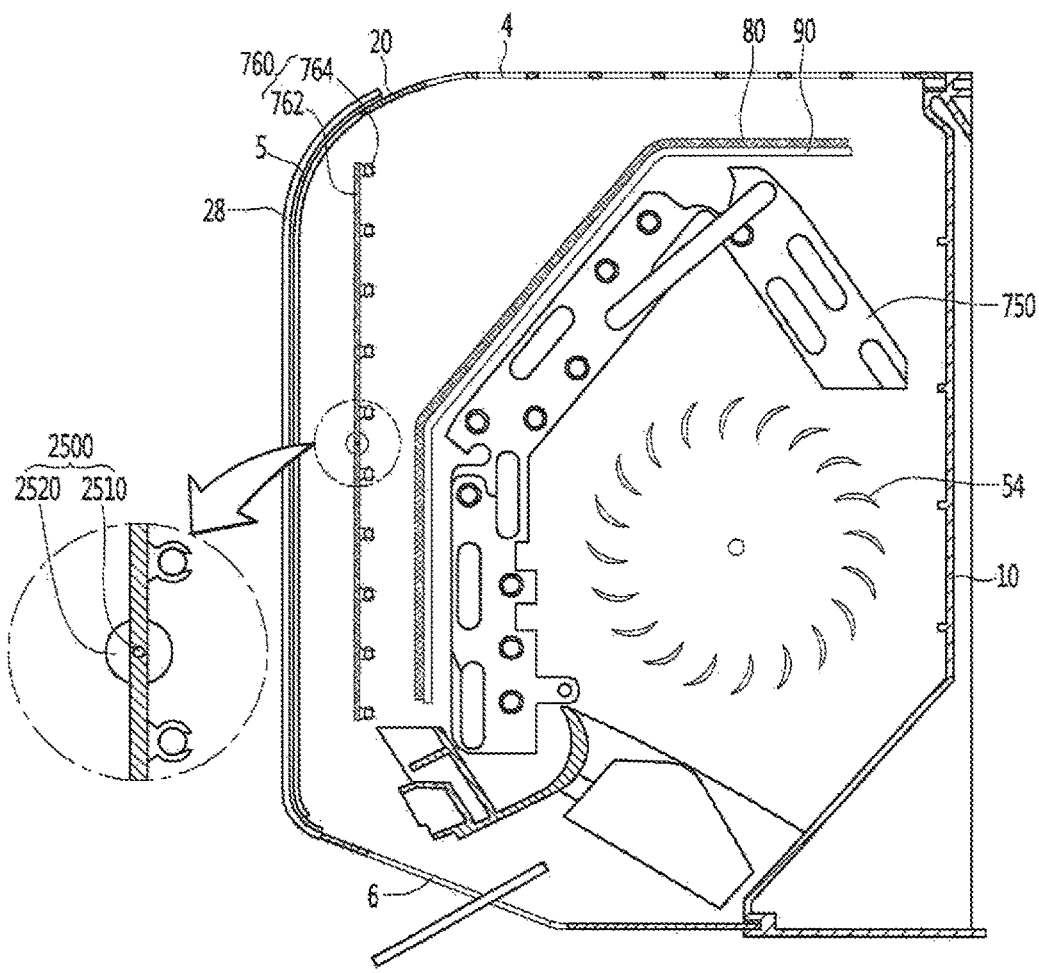
FIGS. 25 to 27 illustrate an embodiment of a porous main body rotation mechanism of a UV sterilization module.
Figure 26:
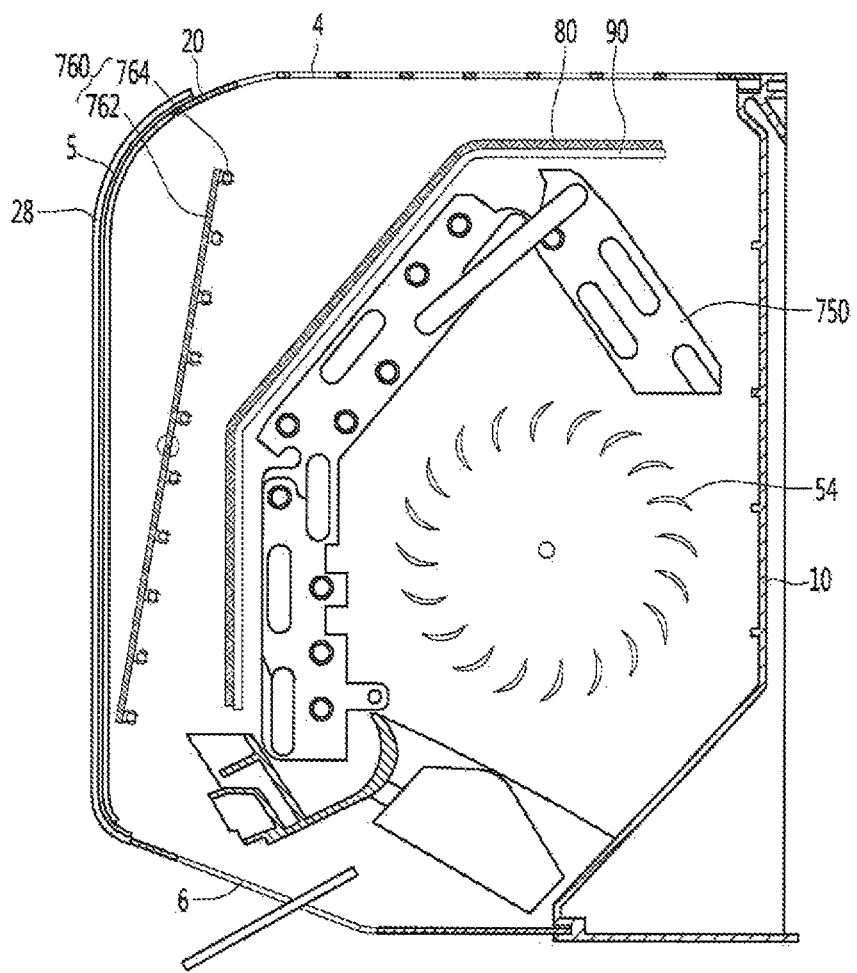
Figure 27:
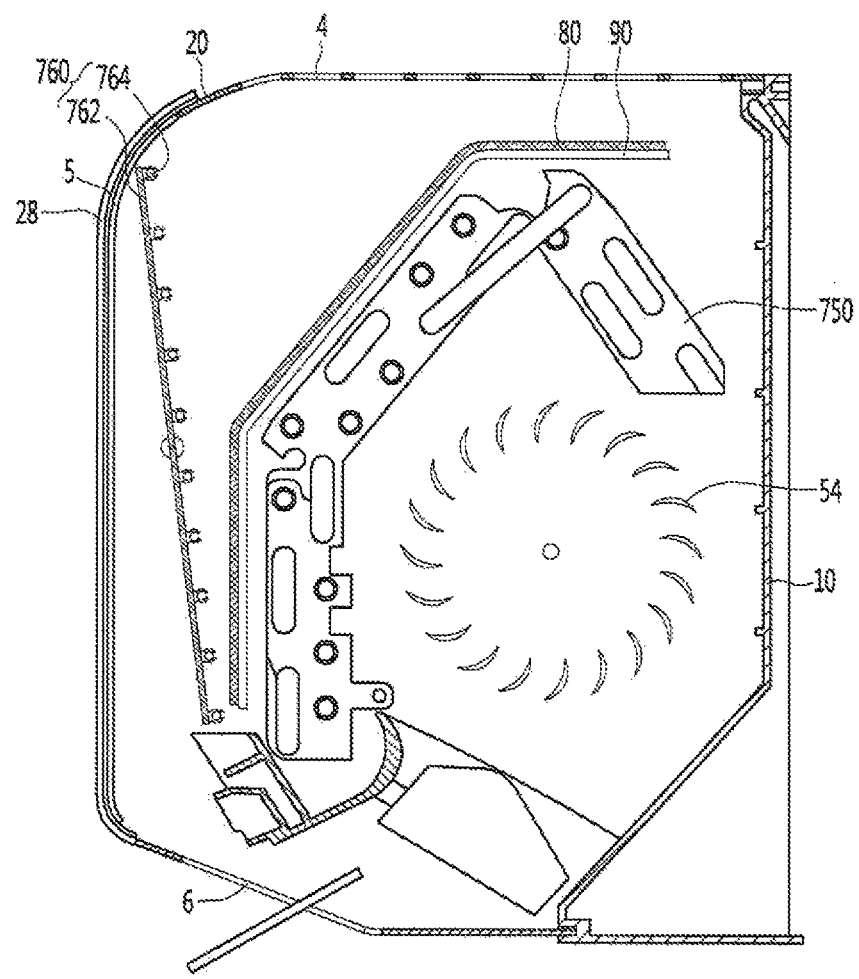

FIGS. 25 to 27 illustrate an embodiment of a porous main body rotation mechanism of a UV sterilization module. The air conditioner according to embodiments may have a porous main body rotation mechanism 2500 to rotate the porous main body 762. The porous main body rotation mechanism 2500 may have a rotation axis 2510 coupled to the porous main body 762. The porous main body rotation mechanism 2500 may be implemented as a motor 2520 having the rotation axis 2510 or a motor 2520 coupled to the rotation axis 2510.

The rotation axis 2510 may be oriented in a horizontal direction. In this way, the porous main body 762 may rotate around the rotation axis 2510. During the rotation of the porous main body 762, the plurality of UV lamps 764 may move toward or away from the heat exchanger 750. For example, among the plurality of UV lamps 764, an upper UV lamp 764 may move toward the heat exchanger 750 while a lower UV lamp 764 may move away from the heat exchanger 750.

The rotation axis 2510 may be oriented in a vertical direction. In this way, the porous main body 762 may rotate around the rotation axis 2510. During the rotation of the porous main body 762, the plurality of UV lamps 764 may move toward or away from the heat exchanger 750. For example, among the plurality of UV lamps 764, a left or first UV lamp 764 may move toward the heat exchanger 750 while a right or second UV lamp 764 may move away from the heat exchanger 750.

Figure 28:
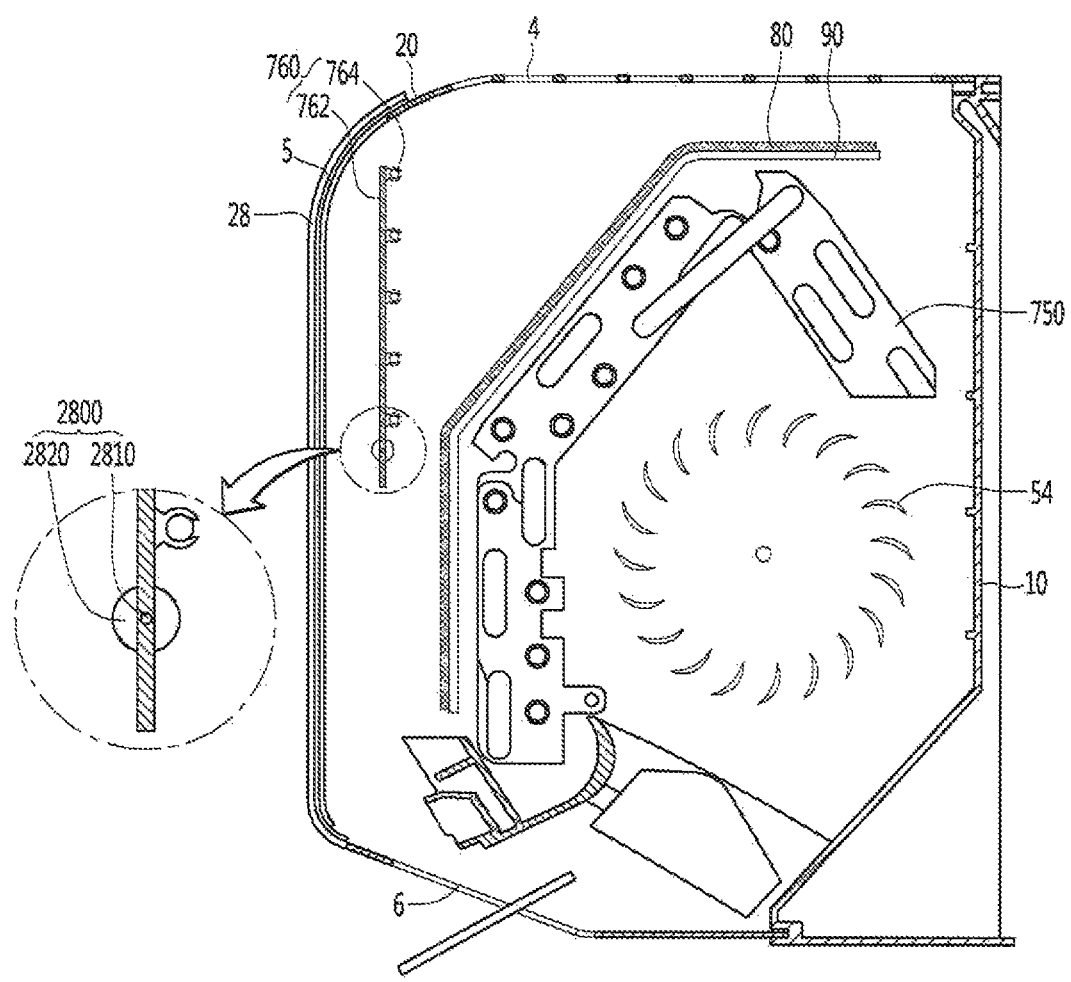
FIGS. 28 to 30 illustrate another embodiment of a porous main body rotation mechanism of a UV sterilization module.
Figure 29:
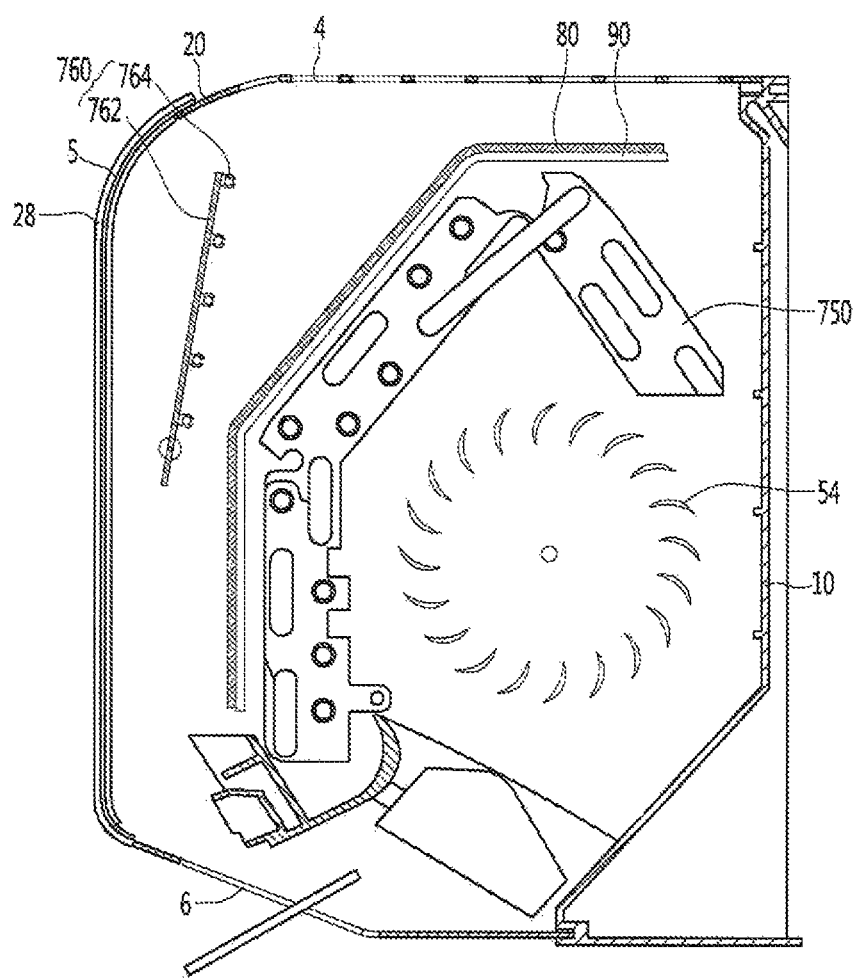
Figure 30:
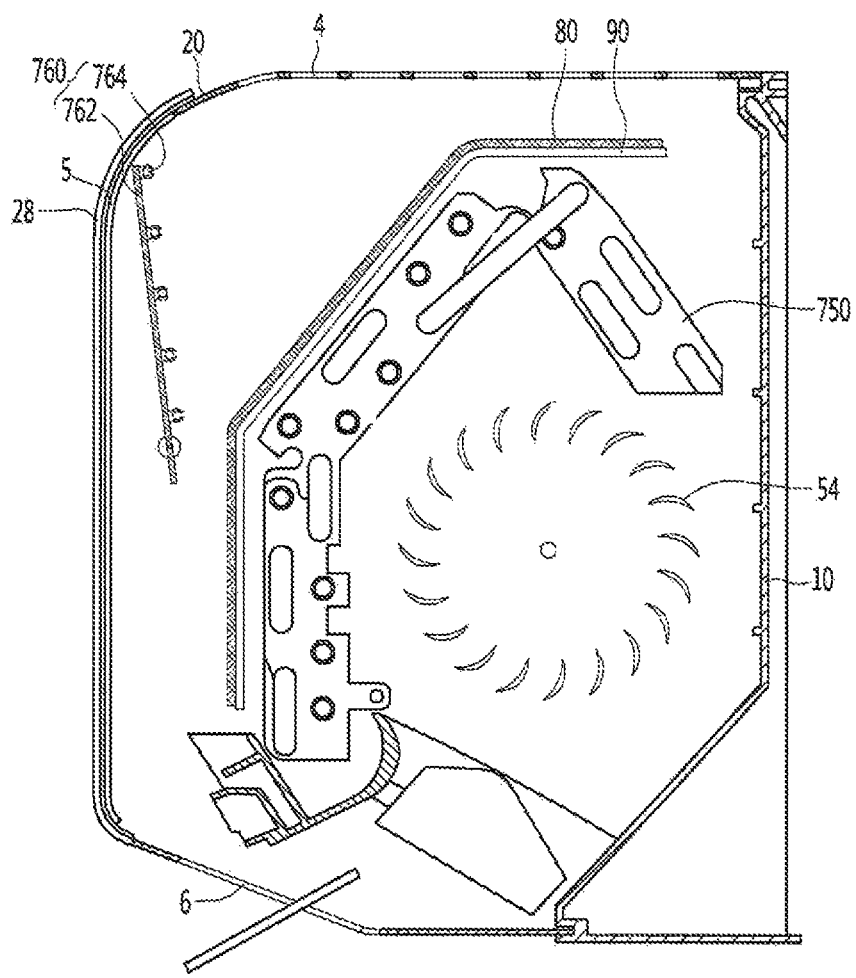

FIGS. 28 to 30 illustrate another embodiment of a porous main body rotation mechanism of a UV sterilization module. The air conditioner may have a porous main body rotation mechanism 2800 to rotate the porous main body 762. The porous main body rotation mechanism 2800 may have a rotation axis 2810 coupled to the porous main body 762. The porous main body rotation mechanism 2800 may be implemented as a motor 2820 having the rotation axis 2810 or a motor 2820 coupled to the rotation axis 2810.

The porous main body rotation mechanism 2800 as shown in FIGS. 28 to 30 may be different from the porous main body rotation mechanism 2500 as shown in FIGS. 25 to 27 in that the UV lamp 764 may be provided only on an upper portion with respect to the rotation axis 2810 and the porous main body 762 may not be present on a lower portion with respect to the rotation axis 2810.

The rotation axis 2810 may be oriented in a horizontal direction. In this way, the porous main body 762 may rotate around the rotation axis 2810. During the rotation of the porous main body 762, the plurality of UV lamps 764 may move toward or away from the heat exchanger 750.

The porous main body rotation mechanism 2800 as shown in FIGS. 28 to 30 may be different from the porous main body rotation mechanism 2500 as shown in FIGS. 25 to 27 in that the porous main body rotation mechanism 2800 may allow all of the plurality of UV lamps to move toward or away from the heat exchanger 750 concurrently.

The air conditioners, configurations, and methods of the embodiments described above are not limitedly applied, but rather, all or a part of the embodiments may be selectively combined so as to achieve various modifications.

Embodiments disclosed herein remove interference with an air channel by a lamp support body. Further, embodiments disclosed herein overcome a problem in that air around a heat exchanger is not sterilized uniformly when a single UV lamp is fixedly provided in one region of an air conditioner. Furthermore, embodiments disclosed herein overcome a problem in that air entering into an air inlet is concentrated at a partial region of a heat exchanger. Additionally, embodiments disclosed herein facilitate an electrical connection between a UV lamp and a body when the lamp is an external electrode lamp type.

Embodiments disclosed herein provide a porous main body with a plurality of holes defined therein to act as a lamp supporter. Further, embodiments disclosed herein provide a parallel connection of a plurality of smaller UV lamps than a conventional UV lamp may on one surface of the porous main body. A smaller UV lamp with a smaller diameter than a diameter of the conventional UV lamp may be provided as an external electrode lamp type for application to a wall-mounted air conditioner.

Embodiments disclosed herein provide a porous main body with a plurality of holes with a same shape and size disposed or provided around an air inlet. Embodiments disclosed herein provide a holder provided at each of both sides of the porous main body for an electrical connection and easy positioning of the external electrode UV lamp.

Using the porous main body with the plurality of holes, the plurality of UV lamps may be supported and an air flow may be smoothly effected. Using the parallel arrangement of the plurality of smaller UV lamps, the air may be sterilized uniformly along the front of the heat exchanger.

Using the smaller UV lamp with a smaller diameter than that of the conventional UV lamp, which is embodied as an external electrode lamp type, may have a more reduced width in an air flow direction than using a single UV lamp with a larger diameter. Further, the air conditioner may be more compact using the above lamp configuration. For the wall-mounted air conditioner with a small inner space, a space efficiency, life span, and power consumption may be improved.

Using the porous main body with a plurality of holes with the same shape and size, which is disposed or provided around the air inlet, the air entering into the air inlet may be aligned while passing through the plurality of holes. Thus, a concentration of air at a partial region of the plurality of UV lamps may be suppressed. Thus, the plurality of UV lamps may sterilize the air uniformly. Using the holder provided at each of both sides of the porous main body, an electrical connection and positioning of the external electrode UV lamp may be facilitated.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of Illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An air conditioner, comprising:
a main body having an air inlet and an air outlet defined therein;
a filter received in the main body to filter air suctioned into the main body;
a heat exchanger configured to perform heat exchange between a refrigerant and the air suctioned into the main body; and
an ultraviolet (UV) sterilization module configured to sterilize the air suctioned into the main body, wherein the UV sterilization module includes:
a porous main body in a mesh form, wherein the porous main body Includes a photocatalyst coating; and
a plurality of UV lamps, wherein the main body includes a bent portion to allow the porous main body to conform to a shape of the heat exchanger, wherein the plurality of UV lamps is arranged to be spaced from each other between the air Inlet and the heat exchanger, wherein the porous main body is provided upstream of the plurality of UV lamps and the heat exchanger with respect to an airflow direction, and wherein the main body includes:
a chassis; and
a front frame at a front of the chassis, wherein an inner space is defined between the chassis and the front frame, wherein the porous main body is coupled to at least one of the chassis or the front frame, wherein a positional relationship of the porous main body including the photocatalyst coating, the plurality of UV lamps, and the heat exchanger prevents an odorized substance from being attached to the plurality of UV lamps and the heat exchanger, preventing pollution and performance degradation of the plurality of the UV lamps and the heat exchanger.

2. The air conditioner of claim 1, wherein each of the plurality of UV lamps is an external electrode fluorescent lamp.

3. The air conditioner of claim 1, wherein the porous main body includes a plurality of first and second holders on first and second sides of the porous main body, respectively, and wherein each of the plurality of UV lamps is coupled to a pair of the first and second holders.

4. The air conditioner of claim 3, wherein the porous main body includes first and second metal rails on the first and second sides of the porous main body, respectively, and wherein the plurality of first and second holders is provided on the first and second metal rails, respectively.

5. The air conditioner of claim 3, wherein each of the plurality of first and second holders is shaped to surround one of the plurality of UV lamps.

6. The air conditioner of claim 1, further including an inverter to supply power to the plurality of UV lamps concurrently.

7. An air conditioner, comprising:
a main body having an air inlet and an air outlet defined therein;
a filter received in the main body to filter air suctioned into the main body;
a heat exchanger configured to perform heat exchange between a refrigerant and the air suctioned into the main body, wherein the heat exchanger has first and second surfaces on different planes;
a mesh member having a first surface that conforms to a shape of the first surface of the heat exchanger and a second surface that conforms to a shape of the second surface of the heat exchanger, wherein the porous main body Includes a photocatalyst coating; and
a plurality of UV lamps supported on the mesh member, wherein a positional relationship of the mesh member including the photocatalyst coating, the plurality of UV lamps, and the heat exchanger prevents an odorized substance from being attached to the plurality of UV lamps and the heat exchanger, preventing pollution and performance degradation of the plurality of the UV lamps and the heat exchanger.

8. The air conditioner of claim 7, wherein the mesh member includes a plurality of metal holders arranged to be spaced from each other on one surface thereof at a predetermined spacing, and wherein the plurality of UV lamps is coupled to the plurality of the metal holders, respectively.

9. The air conditioner of claim 8, wherein each of the plurality of metal holders is shaped to surround one of the plurality of UV lamps.

10. The air conditioner of claim 9, further including an inverter to supply power to the plurality of metal holders concurrently.

11. An air conditioner, comprising
a main body having an air inlet and an air outlet defined therein;
a filter received in the main body to filter air suctioned into the main body;
a heat exchanger configured to perform heat exchange between a refrigerant and the air suctioned into the main body; and
an ultraviolet (UV) sterilization module configured to sterilize the air suctioned into the main body, wherein the UV sterilization module includes a porous lamp support body and a plurality of UV lamps, wherein the plurality of UV lamps is spaced apart and arranged in a parallel manner between the air inlet and the heat exchanger, wherein the porous lamp support body is provided upstream of the plurality of UV lamps and the heat exchanger with respect to an airflow direction, and wherein the porous lamp support body includes a photocatalyst coating, wherein a positional relationship of the porous lamp support body including the photocatalyst coating, the plurality of UV lamps, and the heat exchanger prevents an odorized substance from being attached to the plurality of UV lamps and the heat exchanger, preventing pollution and performance degradation of the plurality of the UV lamps and the heat exchanger.

12. The air conditioner of claim 11, wherein the porous lamp support body includes first and second metal rails at first and second sides thereof, respectively, and wherein the plurality of UV lamps receives power via the first and second metal rails.

13. The air conditioner of claim 12, further including a plurality of metal holders provided on each of the first and second metal rails.

14. The air conditioner of claim 13, wherein the plurality of UV lamps is coupled to the plurality of metal holders, respectively.

15. An air conditioner, comprising
a main body having an air inlet and an air outlet defined therein;
a filter received in the main body to filter air suctioned into the main body;
a heat exchanger configured to perform heat exchange between a refrigerant and the air suctioned into the main body; and
an ultraviolet (UV) sterilization module configured to sterilize the air suctioned into the main body, wherein the UV sterilization module includes:
a porous main body corresponding in shape to the heat exchanger,
wherein the porous main body Includes a photocatalyst coating; and
a plurality of UV lamps provided on the porous main body, wherein the porous main body is provided upstream of the plurality of UV lamps and the heat exchanger with respect to an airflow direction, wherein a positional relationship of the porous main body including the photocatalyst coating, the plurality of UV lamps, and the heat exchanger prevents an odorized substance from being attached to the plurality of UV lamps and the heat exchanger, preventing pollution and performance degradation of the plurality of the UV lamps and the heat exchanger.

16. The air conditioner of claim 15, wherein the porous main body is provided between the filter and the heat exchanger, and the plurality of UV lamps is provided on a surface of the porous main body facing the heat exchanger.

17. The air conditioner of claim 15, wherein the porous main body is provided between the filter and the air inlet, the filter being adjacent the heat exchanger, and the plurality of UV lamps is provided on a surface of the porous main body facing the filter.

18. An air conditioner, comprising
a main body having an air inlet and an air outlet defined therein;
a filter received in the main body to filter air suctioned into the main body;
a heat exchanger configured to perform heat exchange between a refrigerant and the air suctioned into the main body; and
an ultraviolet (UV) sterilization module configured to sterilize the air suctioned into the main body, wherein the UV sterilization module includes:
a porous main body surrounding a front surface of the heat exchanger with respect to an airflow direction, wherein the porous lamp support body includes a photocatalyst coating; and
a plurality of UV lamps provided on the porous main body, wherein the porous main body is provided upstream of the plurality of UV lamps and the heat exchanger with respect to an airflow direction, and, wherein a positional relationship of the porous main body including the photocatalyst coating, the plurality of UV lamps, and the heat exchanger prevents an odorized substance from being attached to the plurality of UV lamps and the heat exchanger, prevention pollution and performance degradation of the plurality of the UV lamps and the heat exchanger.

19. The air conditioner of claim 18, wherein the porous main body is disposed adjacent the air inlet.

20. The air conditioner of claim 18, wherein the porous main body includes an upper body, a rear body, and a front body disposed adjacent to an upper portion, a rear portion, and a front portion of the main body, respectively.

* * * * *